United States Patent
Yasukawa et al.

(10) Patent No.: US 12,285,652 B2
(45) Date of Patent: Apr. 29, 2025

(54) EXERCISE ASSISTING APPARATUS DISPLAYING DIFFERENCE FROM EXEMPLARY MOTIONS

(71) Applicant: NEC Corporation, Tokyo (JP)

(72) Inventors: Makoto Yasukawa, Tokyo (JP); Kosuke Nishihara, Tokyo (JP); Yuji Ohno, Tokyo (JP)

(73) Assignee: NEC CORPORATION, Tokyo (JP)

( * ) Notice: Subject to any disclaimer, the term of this patent is extended or adjusted under 35 U.S.C. 154(b) by 30 days.

(21) Appl. No.: 18/378,773

(22) Filed: Oct. 11, 2023

(65) Prior Publication Data

US 2024/0033570 A1 Feb. 1, 2024

Related U.S. Application Data

(63) Continuation of application No. 18/269,130, filed as application No. PCT/JP2021/012504 on Mar. 25, 2021.

(51) Int. Cl.
A63B 24/00 (2006.01)

(52) U.S. Cl.
CPC ...... *A63B 24/0062* (2013.01); *A63B 24/0006* (2013.01); *A63B 2024/0012* (2013.01); *A63B 2220/05* (2013.01); *A63B 2220/805* (2013.01); *A63B 2220/836* (2013.01); *A63B 2225/52* (2013.01)

(58) Field of Classification Search
CPC ............ A63B 24/0062; A63B 24/0006; A63B 2024/0012; A63B 2220/05; A63B 2220/805; A63B 2220/836; A63B 2225/52; A63B 69/00; A63B 71/06; G16H 30/40; G16H 20/30; G06T 7/20
See application file for complete search history.

(56) References Cited

U.S. PATENT DOCUMENTS

| 10,956,673 | B1 | 3/2021 | Ramezani et al. |
| 2004/0219498 | A1* | 11/2004 | Davidson ............... A63B 69/00 434/247 |
| 2016/0314352 | A1 | 10/2016 | Matsunaga et al. |

(Continued)

FOREIGN PATENT DOCUMENTS

| JP | 2016-041142 A | 3/2016 |
| JP | 2016-208516 A | 12/2016 |

(Continued)

OTHER PUBLICATIONS

International Search Report for PCT Application No. PCT/JP2021/012504, mailed on Jun. 8, 2021.

*Primary Examiner* — Sundhara M Ganesan
(74) *Attorney, Agent, or Firm* — Sughrue Mion, PLLC

(57) ABSTRACT

An exercise assisting apparatus 1 includes: a division unit 312 configured to divide sample motion information 3231 indicating motions of a sample person doing exercise into a plurality of pieces of motion element information 3235, according to regularity of the motions of the sample person; and a generation unit 314 configured to generate an inference model by causing a pre-trained model 322 to learn time-series antecedent dependency of the plurality of pieces of motion element information, the inference model inferring motions of a target person, based on target motion information 3211 indicating the motions of the target person doing exercise.

9 Claims, 9 Drawing Sheets

(56) References Cited

U.S. PATENT DOCUMENTS

| | | |
|---|---|---|
| 2016/0314818 A1 | 10/2016 | Kirk et al. |
| 2019/0022492 A1 | 1/2019 | Takahashi et al. |
| 2019/0179297 A1* | 6/2019 | Kuroda ................. G06N 20/00 |
| 2021/0082412 A1 | 3/2021 | Kennewick |

FOREIGN PATENT DOCUMENTS

| | | |
|---|---|---|
| JP | 2017-055913 A | 3/2017 |
| JP | 2017-215685 A | 12/2017 |
| JP | 2018-000230 A | 1/2018 |
| JP | 2020-005766 A | 1/2020 |
| JP | 2020-194569 A | 12/2020 |
| WO | 2015/098260 A1 | 7/2015 |

* cited by examiner

321

3212　　　　　　　　　　3211

| INFO ID | MOTION INFORMATION |
|---------|--------------------|
| #1 | xxxxxxx |
| #2 | yyyyyyy |
| #3 | zzzzzzz |
| ... | ... |

3213

| INFO ID | MOTION INFORMATION | GROUND TRUTH LABEL |
|---|---|---|
| #1 | xxxxxxxx | (SQUAT, EXEMPLARY) |
| #2 | xxxxxxxx | (SQUAT, BODY TRUNK LESS LEANING FORWARD) |
| #3 | xxxxxxxx | (SQUAT, KNEES LESS BENT) |
| #4 | xxxxxxxx | (SQUAT, CENTER OF GRAVITY SHIFTING TO RIGHT) |
| ... | ... | ... |

EXERCISE ASSISTING APPARATUS DISPLAYING DIFFERENCE FROM EXEMPLARY MOTIONS

CROSS-REFERENCE TO RELATED APPLICATIONS

This application is a Continuation of U.S. application Ser. No. 18/269,130 filed on Jun. 22, 2023, which is a National Stage Entry of PCT/JP2021/012504 filed on Mar. 25, 2021, the contents of all of which are incorporated herein by reference, in their entirety.

TECHNICAL FIELD

The present disclosure relates to a technical field of an exercise assisting apparatus, an exercise assisting method, and a recording medium that are capable of assisting a person doing exercise.

BACKGROUND ART

Patent Reference 1 describes an example of an exercise assisting apparatus capable of assisting a person doing exercise. Patent Reference 1 describes the exercise assisting apparatus that determines a motion form of the person doing an exercise for rehabilitation, by using a form model generated through machine learning.

Besides, background art references related to the present disclosure include Patent Reference 2.

CITATION LIST

Patent References

Patent Reference 1

Japanese Patent Laid-Open No. 2017-055913 A

Patent Reference 2

Japanese Patent Laid-Open No. 2018-000230 A

SUMMARY OF THE INVENTION

Problem to be Solved by the Invention

Generally, an exercise assisting apparatus uses a form model generated beforehand through machine learning that uses, for training data, data indicating motions of a person doing a certain type of exercise (for example, a squat). On the other hand, there is a possibility that a person assisted by the exercise assisting apparatus does not only the exercise already learned by the form model, but also an exercise that has not yet been learned by the form model. In such a case, it is generally preferable that a new form model be generated through machine learning that uses, for training data, data indicating motions of a person doing the exercise that has not yet been learned by the form model. However, to generate a form model through machine learning, a large quantity of data indicating motions of a person doing an exercise to be learned by the form model is needed. Accordingly, a technical problem arises that it is difficult to easily generate a form model.

Note that not only the form model described in Patent Reference 1, when an inference model, which infers motions of a person from motion information indicating the motions of the person, is generated, a technical problem also arises that it is difficult to easily generate the inference model.

An example object of the present disclosure is to provide an exercise assisting apparatus, an exercise assisting method, and a recording medium that are able to solve the above-described technical problem. As an example, an example object of the present disclosure is to provide an exercise assisting apparatus, an exercise assisting method, and a recording medium that are capable of easily generating an inference model inferring motions of a person.

Means for Solving the Problem

A first aspect of an exercise assisting apparatus in the present disclosure includes: a division unit configured to divide sample motion information indicating motions of a sample person doing exercise into a plurality of pieces of motion element information, according to regularity of the motions of the sample person; and a generation unit configured to generate an inference model by causing a pre-trained model to learn time-series antecedent dependency of the plurality of pieces of motion element information, the inference model inferring motions of a target person, based on target motion information indicating the motions of the target person doing exercise.

A second aspect of an exercise assisting apparatus in the present disclosure includes: acquisition unit configured to acquire an inference model capable of inferring motions of a target person from target motion information indicating the motions of the target person doing exercise; and an inference unit configured to infer the motions of the target person by using the inference model and the target motion information, wherein the inference model is a model generated by dividing sample motion information indicating motions of a sample person doing exercise into a plurality of pieces of motion element information, according to a flow of changes in motion of the sample person, and by causing a pre-trained model to learn time-series antecedent dependency of the plurality of pieces of motion element information.

A first aspect of an exercise assisting method in the present disclosure includes: dividing sample motion information indicating motions of a sample person doing exercise into a plurality of pieces of motion element information, according to regularity of the motions of the sample person; and generating an inference model by causing a pre-trained model to learn time-series antecedent dependency of the plurality of pieces of motion element information, the inference model inferring motions of a target person, based on target motion information indicating the motions of the target person doing exercise.

A second aspect of an exercise assisting method in the present disclosure includes: acquiring an inference model capable of inferring motions of a target person from target motion information indicating the motions of the target person doing exercise; and inferring the motions of the target person by using the inference model and the target motion information, wherein the inference model is a model generated by dividing sample motion information indicating motions of a sample person doing exercise into a plurality of pieces of motion element information, according to a flow of changes in motion of the sample person, and by causing a pre-trained model to learn time-series antecedent dependency of the plurality of pieces of motion element information.

A first aspect of a recording medium in the present disclosure is a recording medium storing a computer program causing a computer to execute an exercise assisting method, the exercise assisting method including: dividing sample motion information indicating motions of a sample person doing exercise into a plurality of pieces of motion element information, according to regularity of the motions of the sample person; and generating an inference model by causing a pre-trained model to learn time-series antecedent dependency of the plurality of pieces of motion element information, the inference model inferring motions of a target person, based on target motion information indicating the motions of the target person doing exercise.

A second aspect of a recording medium in the present disclosure is a recording medium storing a computer program causing a computer to execute an exercise assisting method, the exercise assisting method including: acquiring an inference model capable of inferring motions of a target person from target motion information indicating the motions of the target person doing exercise; and inferring the motions of the target person by using the inference model and the target motion information, wherein the inference model is a model generated by dividing sample motion information indicating motions of a sample person doing exercise into a plurality of pieces of motion element information, according to a flow of changes in motion of the sample person, and by causing a pre-trained model to learn time-series antecedent dependency of the plurality of pieces of motion element information.

Advantageous Effects of the Invention

According to the exercise assisting apparatus, the exercise assisting method, and the recording medium as described above, it is possible to take into consideration a flow of changes in motion of a person when an inference model inferring motions of the person from motion information indicating the motions of the person is generated, or to use such an inference model generated with a flow of changes in motion of a person taken into consideration.

is a plane view showing.

DESCRIPTION OF EXAMPLE EMBODIMENTS

Hereinafter, an example embodiment of an exercise assisting apparatus, an exercise assisting method, and a recording medium is described with reference to the drawings. In the following, an exercise assisting system SYS is described to which the example embodiment of the exercise assisting apparatus, the exercise assisting method, and the recording medium is applied.

(1) Configuration of Exercise Assisting System SYS

First, a configuration of the exercise assisting system SYS according to the present example embodiment is described.

(1-1) Entire Configuration of Exercise Assisting System SYS

Figure 1:
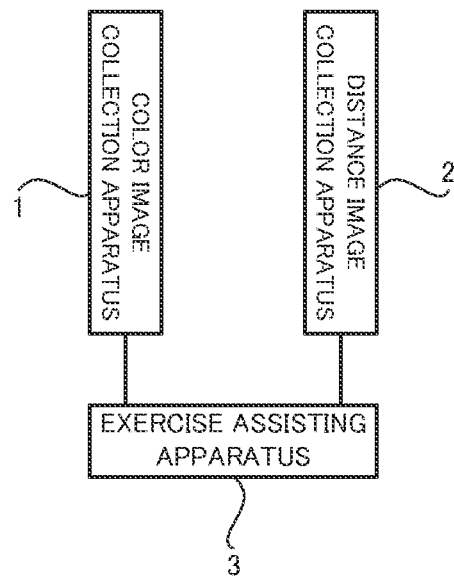
FIG. 1 is a block diagram showing an entire configuration of an exercise assisting system according to an example embodiment.

First, the entire configuration of the exercise assisting system SYS according to the present example embodiment is described with reference to FIG. 1. FIG. 1 is a block diagram showing the entire configuration of the exercise assisting system SYS according to the present example embodiment.

The exercise assisting system SYS performs exercise assisting processing for assisting a target person who is doing an exercise. For example, the exercise assisting processing may include processing of assisting the target person in such a manner that the target person can do the appropriate exercise. For example, the exercise assisting processing may include processing of assisting the target person in such a manner that motions of the target person doing the exercise approximate or match exemplary motions (in other words, motions serving as an exemplar, or ideal motions). For example, the exercise assisting processing may include processing of assisting the target person in such a manner that motions of the target person doing the exercise approximate or match the exemplary motions, by notifying the target person of a displacement between the actual motions of the target person and the exemplary motions.

An example of the exercise is an exercise for rehabilitation. An example of the target person who does the exercise for rehabilitation is a patient in a medical institution. In such a case, the exercise assisting system SYS may assist the patient in such a manner that the patient can do the appropriate exercise for rehabilitation. The exercise assisting system SYS may assist the patient in such a manner that motions of the patient approximate or match exemplary motions for bringing about an effect of rehabilitation. Note that a patient in the present example embodiment may refer to a person receiving a medical service of rehabilitation in a medical institution. Medical institutions in the present example embodiment may include not only an institution where so-called medical practice takes place (for example, at least one of a hospital and a clinic), but also an arbitrary institution that does not perform medical practice but provides a medical service related to rehabilitation (for example, at least one of a healthcare facility for elderly people who need geriatric care, a welfare facility for elderly people, and an office of a home visiting rehabilitation provider).

Another example of the exercise is an exercise for practicing a sport. An example of the target person who does the exercise for practicing a sport is an athlete (for example, at least one of an amateur and a professional) involved in the sport. In such a case, the exercise assisting system SYS may assist the athlete in such a manner that the athlete can do the appropriate exercise for practice. The exercise assisting system SYS may assist the athlete in such a manner that motions of the athlete approximate or match exemplary motions to the athlete.

Another example of the exercise is an exercise for workout to get in shape. In such a case, an example of the target person who does the exercise for workout is a member of a workout facility (for example, at least one of a training gym and a fitness gym). In such a case, the exercise assisting system SYS may assist the member in such a manner that the member can do the appropriate exercise for workout. The exercise assisting system SYS may assist the member in such a manner that motions of the member approximate or match exemplary motions for bringing about an effect of workout.

In the present example embodiment, since the exercise assisting system SYS assists the target person, the target person may do the exercise in a place out of sight of an assistant for assisting the target person (that is, a place where the assistant cannot pay sufficient attention to the target person). In other words, the exercise assisting system SYS may assist the target person who is doing the exercise in the place out of sight of the assistant. However, the exercise assisting system SYS may assist the target person who is doing the exercise in a place within sight of the assistant.

When the target person is a patient who does the exercise for rehabilitation, assistants may include a healthcare worker. The assistants may include, in particular, a healthcare worker engaged in rehabilitation. Note that "healthcare workers" in the present example embodiment may refer to people in general who are engaged in healthcare that is activities aimed at at least one of curing illness, preventing illness, maintaining good health, restoring health, and improving health. The healthcare workers may include at least one of a doctor, a dentist, a midwife, an allied professional (for example, at least one of a nurse, a physical therapist, and the like), and the like. When the target person is an athlete who does the exercise for practicing a sport, assistants may include an instructor of the sport. When the target person is an amateur athlete who does the exercise for practicing a sport, assistants may include a professional athlete involved in the sport. When the target person is a member who does the exercise for workout to get in shape, assistants may include a trainer at a workout facility.

In order to perform the exercise assisting processing, the exercise assisting system SYS includes a color image collection apparatus 1, a distance image collection apparatus 2, and an exercise assisting apparatus 3 as shown in FIG. 1.

The color image collection apparatus 1 is an image pickup apparatus capable of picking up an image of a target person. The color image collection apparatus 1 generates a color image in which the target person appears, by picking up an image of the target person. The color image collection apparatus 1 generates a plurality of color images by picking up an image of the target person in each predetermined image pickup period. For example, the color image collection apparatus 1 may generate 30 color images during a one-second period by picking up an image of the target person 30 times a second. Note that a color image in the present example embodiment includes a plurality of pixels, and may refer to an image in which an RGB value of an object (for example, part of the target person) appearing at each pixel is associated with the pixel.

Note that in addition to, or instead of, the color image collection apparatus 1, the exercise assisting system SYS may include an image collection apparatus that generates an arbitrary image in which the target person appears, by picking up an image of the target person. The image generated by the image collection apparatus may be an image with a different property from that of the color image. As an example, the image generated by the image collection apparatus may be a monochrome image.

The distance image collection apparatus 2 is an image pickup apparatus capable of picking up an image of the target person. The distance image collection apparatus 2 generates a distance image in which the target person appears, by picking up an image of the target person. To generate the distance image, the distance image collection apparatus 2 may pick up an image of the target person by using, for example, a time-of-flight method. However, a method used by the distance image collection apparatus 2 is not limited to the time-of-flight method. The distance image collection apparatus 2 may pick up an image of the target person by using a different method from the time-of-flight method. The distance image collection apparatus 2 generates a plurality of distance images by picking up an image of the target person in each predetermined image pickup period. For example, the distance image collection apparatus 2 may generate 30 distance images during a one-second period by picking up an image of the target person 30 times a second. The distance image collection apparatus 2 may pick up an image of the target person in synchronization with a timing at which the color image collection apparatus 1 picks up an image of the target person. Note that a distance image in the present example embodiment includes a plurality of pixels, and may refer to an image in which a distance between an object (for example, part of the target person) appearing at each pixel and the distance image collection apparatus 2 is associated with the pixel.

Note that instead of including the color image collection apparatus 1 and the distance image collection apparatus 2 separately, the exercise assisting system SYS may include a single image collection apparatus that is capable of functioning as the color image collection apparatus 1 and is capable of functioning as the distance image collection apparatus 2.

The exercise assisting apparatus 3 actually performs the exercise assisting processing. Specifically, the exercise assisting apparatus 3 acquires a color image from the color image collection apparatus 1. Moreover, the exercise assisting apparatus 3 acquires a distance image from the distance image collection apparatus 2. Thereafter, the exercise assisting apparatus 3 performs the exercise assisting processing for assisting the target person, by using the acquired color image and distance image.

(1-2) Configuration of Exercise Assisting Apparatus 3

Figure 2:
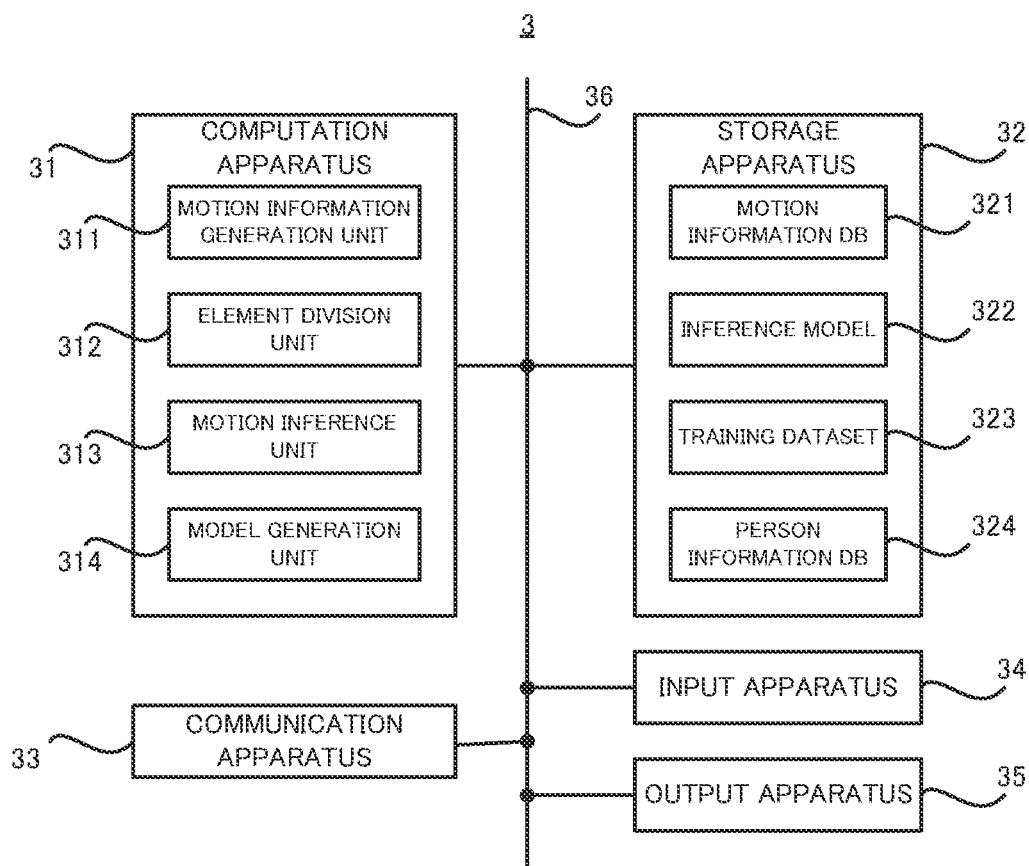
FIG. 2 is a block diagram showing a configuration of an exercise assisting apparatus in the present example embodiment.

Next, a configuration of the exercise assisting apparatus 3 is described with reference to FIG. 2. FIG. 2 is a block diagram showing the configuration of the exercise assisting apparatus 3.

As shown in FIG. 2, the exercise assisting apparatus 3 includes a computation apparatus 31 and a storage apparatus 32. Further, the exercise assisting apparatus 3 includes a communication apparatus 33, an input apparatus 34, and an output apparatus 35. However, the exercise assisting apparatus 3 may omit to include at least one of the communication apparatus 33, the input apparatus 34, and the output apparatus 35. The computation apparatus 31, the storage apparatus 32, the communication apparatus 33, the input apparatus 34, and the output apparatus 35 may be connected through a data bus 36.

The computation apparatus 31 includes, for example, a CPU (Central Processing Unit). The computation apparatus 31 reads a computer program. For example, the computation apparatus 31 may read the computer program stored in the storage apparatus 32. For example, the computation apparatus 31 may read the computer program stored in a computer-readable non-transitory recording medium, by using the input apparatus 34 capable of functioning as a recording medium reading apparatus. The computation apparatus 31 may acquire (that is, may download or may read) the computer program, via the communication apparatus 33, from an undepicted apparatus disposed outside of the exercise assisting apparatus 3. The computation apparatus 31 executes the read computer program. As a result, a logical functional block for performing an operation to be performed by the exercise assisting apparatus 3 (for example, at least part of the exercise assisting processing) is implemented in the computation apparatus 31. In other words, the computation apparatus 31 is capable of functioning as a controller for implementing the logical functional block for performing the operation to be performed by the exercise assisting apparatus 3.

FIG. 2 shows examples of the logical functional block implemented in the computation apparatus 31 in order to perform at least part of the exercise assisting processing. As shown in FIG. 2, a motion information generation unit 311, an element division unit 312, and a motion inference unit 313 are implemented in the computation apparatus 31.

The motion information generation unit 311 generates motion information 3211 indicating motions of a target person, based on a distance image. For example, the motion information generation unit 311 generates the motion information 3211 indicating motions of the target person along a time series, based on a plurality of distance images generated by consecutively picking up images of the target person.

Figures 3, 4:
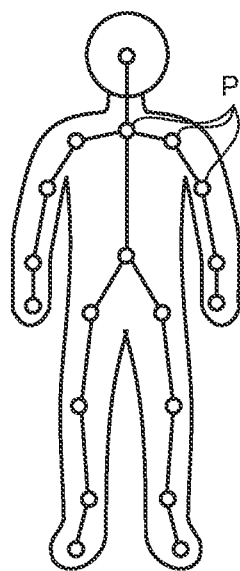
FIG. 3 is a plane view showing an example of a template representing a human body.
FIG. 4 shows an example of a data structure of motion information.

Specifically, the motion information generation unit 311 performs template matching processing using a template representing a human body, for one distance image generated by picking up an image of the target person at a certain time. An example of the template representing a human body is shown in FIG. 3. As shown in FIG. 3, the template may include information related to a surface of the human body and information related to a plurality of joints P that forms a skeleton of the human body. The motion information generation unit 311 may perform template matching by deforming the template in such a manner that at least part of the surface of the body represented by the template is positioned on a surface of skin of the target person appearing in the distance image. The motion information generation unit 311 may perform template matching by deforming the template in such a manner that at least part of the surface of the body represented by the template is positioned on a surface of clothes worn by the target person appearing in the distance image. With deformation of the template, the plurality of joints P shown by the template also comes to the positions of the plurality of joints of the target person appearing in the distance image, respectively. As a result, the motion information generation unit 311 can calculate coordinate values indicating the position of each joint P forming the skeleton of the target person on a coordinate system of the distance image. Thereafter, the motion information generation unit 311 translates the coordinate values indicating the positions of the joints P on the coordinate system of the distance image, into coordinate values indicating the positions of the joints P on a coordinate system of a space in which the target person is doing an exercise. The motion information generation unit 311 repeats similar operations for a plurality of distance images generated by consecutively picking up images of the target person. As a result, the motion information generation unit 311 generates a set of coordinate values indicating the positions of the plurality of joints P at a plurality of times when the plurality of distance images is generated, respectively (that is, a time series of coordinate values indicating the positions of the plurality of joints P), as the motion information 3211 indicating motions of the target person along a time series.

The motion information generation unit 311 may store the generated motion information 3211 in a motion information DB (DataBase) 321. The motion information DB 321 is stored in the storage apparatus 32. An example of a data structure of the motion information DB 321 is shown in FIG. 4. As shown in FIG. 4, the motion information DB 321 may store a motion information record 3213 including motion information 3211 and an information ID 3212 for identifying the motion information 3211.

The motion information DB 321 may store a plurality of such motion information records 3213. For example, the distance image collection apparatus 2 picks up images of a plurality of different target persons, in some cases. In such a case, the motion information DB 321 may store a plurality of motion information records 3213 corresponding to the plurality of different target persons, respectively. For example, the motion information DB 321 may store a motion information record 3213 including motion information 3211 indicating motions of a first target person, and a motion information record 3213 including motion information 3211 indicating motions of a second target person individually. For example, the distance image collection apparatus 2 picks up images of the same target person at a plurality of different times, in some cases. In such a case, the motion information DB 321 may store a plurality of motion information records 3213 corresponding respectively to the plurality of times at each of which an image of the same target person is picked up. For example, the motion information DB 321 may store a motion information record 3213 including motion information 3211 indicating motions of the target person at a first time, and a motion information record 3213 including motion information 3211 indicating motions of the target person at a second time individually. For example, the distance image collection apparatus 2 consecutively picks up images of the target person who is repeating the same exercise, in some cases. In other words, the distance image collection apparatus 2 consecutively picks up images of the target person who continues doing the same exercise multiple times, in some cases. In such a case, the motion information DB 321 may store a plurality of motion information records 3213 corresponding respectively to the plurality of times of the exercise done by the same target person. For example, the motion information DB 321 may store a motion information record 3213 including motion information 3211 indicating motions of the target person doing the exercise the first time (for example, a first squat), and a motion information record 3213 including motion information 3211 indicating motions of the target person doing the exercise the second time (for example, a second exercise) subsequent to the first-time exercise individually.

Referring again to FIG. 2, the element division unit 312 divides the motion information 3211 generated by the motion information generation unit 311 into a plurality of pieces of motion element information 3214, according to regularity (in other words, periodicity) in the motions of the target person. For example, regularity is seen in motions of a target person doing a certain exercise, in many cases. In such a case, if such regularity in the motions of the target person is taken into consideration, it is presumed that a series of the motions of the target person doing the certain exercise can be classified into a plurality of motions (hereinafter, referred to as "motion elements") along a time series. With such regularity in the motions of the target person taken into consideration, the element division unit 312 divides the motion information 3211 into the plurality of pieces of motion element information 3214, which indicates a plurality of motion elements, respectively.

Figure 5:
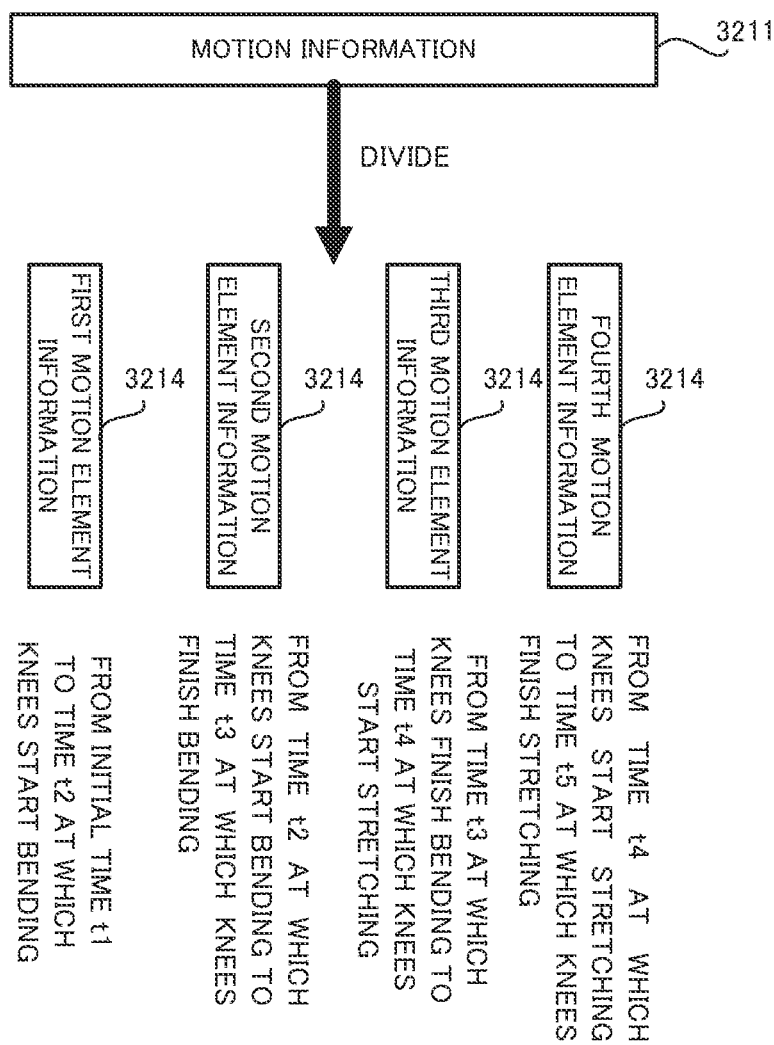
FIG. 5 shows a plurality of pieces of motion element information generated by dividing the motion information.

For example, motions of a target person who is doing squats as an example of the exercise change from a first state in which the target person is in a standing posture, to a second state in which the target person gradually bends the knees, and to a third state in which the target person stays still after finishing bending the knees, and return to the first state via a fourth state in which the target person gradually stretches the knees. In such a case, the following regularity is seen in the motions of the target person: the motions of the target person begin from the first state and, via the second, third, and fourth states, return to the first state. Accordingly, in the case in question, the motions of the target person can be classified into a first motion element of the target person being still in a standing posture, a second motion element of the target person gradually bending the knees, a third motion element of the target person staying still after finishing bending the knees, and a fourth motion element of the target person gradually stretching the knees. Accordingly, when the target person is doing squats as an example of the exercise, the element division unit 312 may divide the motion information 3211 into (i) motion element information 3214 indicating the first motion element of the target person being still in a standing posture, (ii) motion element information 3214 indicating the second motion element of the target person gradually bending the knees, (iii) motion element information 3214 indicating the third motion element of the target person staying still after finishing bending the knees, and (iv) motion element information 3214 indicating the fourth motion element of the target person gradually stretching the knees, as shown in FIG. 5.

When it is taken into consideration that a series of motions of a target person doing a certain exercise can be classified into a plurality of motion elements along a time series, the processing of dividing the motion information 3211 into the plurality of pieces of motion element information 3214 may be regarded as equivalent to processing of dividing the motion information 3211 along a time series. For example, in the example shown in FIG. 5, the element division unit 312 may divide the motion information 3211 into (i) the motion element information 3214 indicating, as the first motion element, a motion of the target person during a period from an initial time t1 to a time t2 at which the target person starts bending the knees, (ii) the motion element information 3214 indicating, as the second motion element, a motion of the target person during a period from the time t2 at which the target person starts bending the knees to a time t3 at which the target person finishes bending the knees, (iii) the motion element information 3214 indicating, as the third motion element, a motion of the target person during a period from the time t3 at which the target person finishes bending the knees to a time t4 at which the target person starts stretching the knees, and (iv) the motion element information 3214 indicating, as the fourth motion element, a motion of the target person during a period from the time t4 at which the target person starts stretching the knees to a time t5 at which the target person finishes stretching the knees. Note that the time t5 at which the target person finishes stretching the knees may be regarded as equivalent to the initial time t1.

Referring again to FIG. 2, the motion inference unit 313 infers the motions of the target person, by using the plurality of pieces of motion element information 3214 generated by the element division unit 312. The processing of inferring the motions of the target person may include, for example, processing of inferring whether or not the motions of the target person are exemplary motions. The processing of inferring the motions of the target person may include, for example, processing of inferring a difference (that is, a displacement) between the motions of the target person and the exemplary motions.

Figure 6:
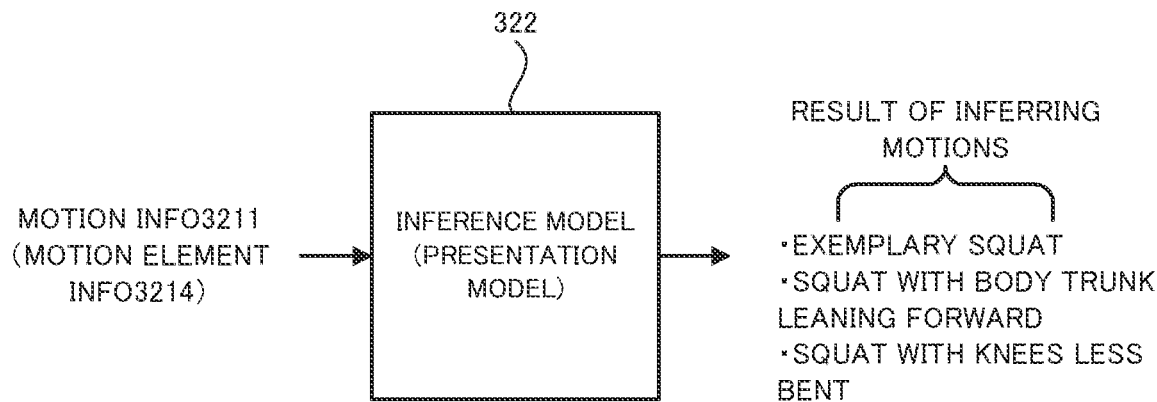
FIG. 6 conceptually shows an inference model.

In the present example embodiment, the motion inference unit 313 infers the motions of the target person by using the plurality of pieces of motion element information 3214 and an inference model 322. The inference model 322 is a model capable of inferring motions of a target person from motion information 3211 (specifically, a plurality of pieces of motion element information 3214 generated by dividing the motion information 3211). For example, as shown in FIG. 6, the inference model 322 may be a model capable of outputting a result of inferring motions of a target person when motion information 3211 (specifically, a plurality of pieces of motion element information 3214 generated by dividing the motion information 3211) is inputted. In the example shown in FIG. 6, the inference model 322 outputs a result of inferring the motions of the target person who is doing squats, which are an example of the exercise. For example, the inference model 322 may output an inference result obtained by inferring whether the motions of the target person are motions corresponding to an exemplary squat, are motions corresponding to a squat with the body trunk less leaning forward as compared to the exemplary squat, or are motions corresponding to a squat with the knees less bent as compared to the exemplary squat. For example, the inference model 322 may output an inference result obtained by inferring a difference between the motions of the target person and the motions corresponding to the exemplary squat.

Figure 7:
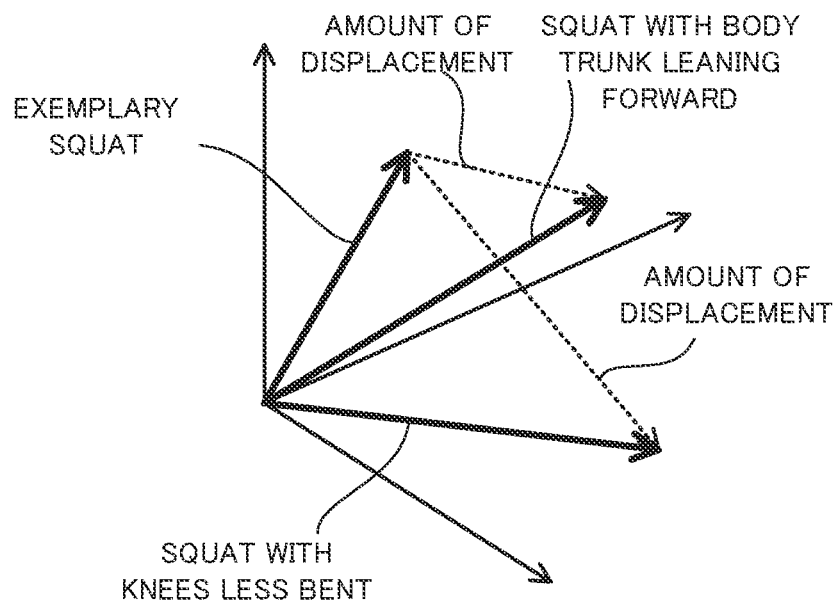
FIG. 7 conceptually shows a presentation space (vector space) defined by the inference model.

The inference model 322 may be considered to define a presentation space (vector space) for presenting the motion information 3211 by using a vector (that is, presenting the motions of the target person by using a vector), as shown in FIG. 7. In other words, the inference model 322 may be considered to define a presentation space (coordinate space) for presenting the motion information 3211 by using coordinate values (that is, presenting the motions of the target person by using coordinate values) indicated by a vector. In such a case, the processing of inferring the motions of the target person by using the motion information 3211 and the inference model 322 may be regarded as processing of identifying a vector representing the motion information 3211 (that is, a vector representing the motions of the target person) in the presentation space. The processing of inferring the motions of the target person by using the motion information 3211 and the inference model 322 may be regarded as processing of identifying coordinate values indicated by a vector representing the motion information 3211 (that is, coordinate values representing the motions of the target person) in the presentation space.

The example shown in FIG. 7 illustrates the presentation space defined by the inference model 322 that outputs a result of inferring the motions of the target person doing squats, which are an example of the exercise. In such a case, as shown in FIG. 7, a vector (coordinate values) representing the motions corresponding to the exemplary squat, a vector (coordinate values) representing the motions corresponding to the squat with the body trunk less leaning forward as compared to the exemplary squat, and a vector (coordinate values) representing the motions corresponding to the squat with the knees less bent as compared to the exemplary squat are, typically, mutually different vectors in the presentation space. As a result, a difference between the vector (coordinate values) representing the exemplary motions and a vector (coordinate values) representing the actual motions of the target person inferred by the inference model 322 can be said to indicate a property of a displacement (for example, at least one of a type of the displacement and an amount of the displacement) of the actual motions of the target person from the exemplary motions. For example, in the example shown in FIG. 7, a difference between the vector (coordinate values) representing the motions corresponding to the exemplary squat and the vector (coordinate values) representing the motions corresponding to the squat with the body trunk less leaning forward as compared to the exemplary squat can be said to indicate an amount of displacement of an amount of leaning forward of the body trunk in the actual motions of the target person from an amount of leaning forward of the body trunk in the exemplary motions. Since the difference between the vector (coordinate values) representing the exemplary motions and the vector (coordinate values) representing the actual motions of the target person inferred by the inference model 322 in the presentation space indicates a property of the displacement of the actual motions of the target person from the exemplary motions as described above, the inference model 322 may be considered to output, as the result of inferring the motions of the target person, information including the property of the displacement of the actual motions of the target person from the exemplary motions.

The inference model 322 is a model capable of being trained (in other words, capable of being built, capable of being generated, or capable of being updated) through training processing (typically, training processing based on machine learning). An example of the model capable of being trained is a model using a neural network. In such a case, the training processing for training the inference model 322 may include processing for learning a parameter (that is, setting, determining, or updating a parameter) of the neural network included in the inference model 322.

Motion information 3211 (a plurality of pieces of motion element information 3214) to be inputted into the inference model 322 is, as described above, information indicating motions of a target person along a time series, and therefore corresponds to time-series data. Accordingly, the inference model 322 is a model capable of inferring motions of a target person, based on antecedent dependency in motion information 3211 that is time-series data (that is, antecedent dependency of a plurality of pieces of motion element information 3214). In other words, the inference model 322 is a model capable of taking into consideration antecedent dependency in motion information 3211 that is time-series data (that is, antecedent dependency of a plurality of pieces of motion element information 3214) in order to infer motions of a target person. However, the inference model 322 may be a different model from the model capable of inferring motions of a target person based on antecedent dependency in motion information 3211 that is time-series data (that is, antecedent dependency of a plurality of pieces of motion element information 3214).

An example of the inference model 322 capable of taking into consideration antecedent dependency of a plurality of pieces of motion element information 3214 as described above is a model using BERT (Bidirectional Encoder Representations from Transformer). Although Bert is a model used mainly for natural language processing, it is possible in the present example embodiment to use Bert in order to process arbitrary time-series data that is different from a language. Bert is a bidirectional neural network in which an output of an intermediate layer into which input data at a first time is inputted is inputted into each of an intermediate layer into which input data at a second time later than the first time is inputted, and an intermediate layer into which input data at a third time earlier than the first time is inputted. Another example of a bidirectional neural network is a bidirectional recurrent neural network. Accordingly, another example of the inference model 322 is a model using a bidirectional recurrent neural network. However, for the inference model 322, a model may be used that uses an ordinary recurrent neural network in which whereas an output of an intermediate layer into which input data at a first time is inputted is inputted into an intermediate layer into which input data at a second time later than the first time is inputted, the output is not inputted into an intermediate layer into which input data at a third time earlier than the first time is inputted. Also in such a case, it remains the same that the inference model 322 is a model capable of inferring motions of a target person, based on antecedent dependency in motion information 3211 that is time-series data (that is, antecedent dependency of a plurality of pieces of motion element information 3214).

Figures 8, 9:
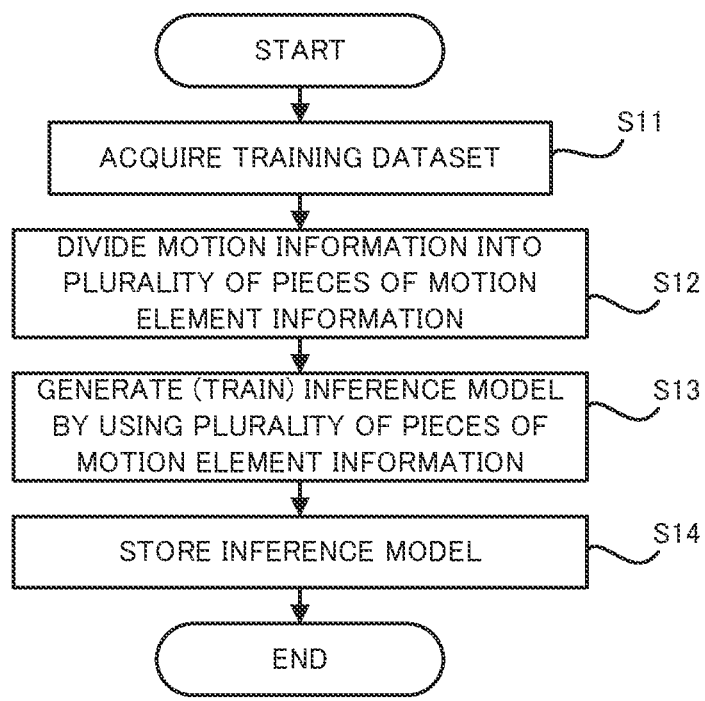
FIG. 8 shows an example of a data structure of a training dataset.
FIG. 9 is a flowchart showing a flow of pre-training processing.

When the inference model 322 is a model capable of being trained, the exercise assisting apparatus 3 may perform the training processing for training the inference model 322, in addition to the exercise assisting processing. In the present example embodiment, the exercise assisting apparatus 3 may perform pre-training processing as the training processing. The pre-training processing is performed by using a training dataset 323. An example of a data structure of the training dataset 323 is shown in FIG. 8. As shown in FIG. 8, the training dataset 323 may store a plurality of (typically, a large number of) training data records 3234, each including motion information 3231, a ground truth label 3232, and an information ID 3233 for identifying the motion information 3231.

The motion information 3231 may be different from the above-described motion information 3211 indicating motions of a target person, in that the motion information 3231 may indicate motions of an arbitrary person who is not subjected to the exercise assisting processing, in addition to, or instead of, motions of a target person who is subjected to the exercise assisting processing. The other characteristics of the motion information 3231 may be the same as the other characteristics of the motion information 3211. In such a case, the training dataset 323 may include a training data record 3234 including motion information 3231 indicating motions of a target person who is subjected to the exercise assisting processing. In other words, the training dataset 323 may include a training data record 3234 including, as motion information 3231, motion information 3211 generated through the exercise assisting processing. Further, the training dataset 323 may include a training data record 3234 including motion information 3231 indicating motions of an arbitrary person who is not subjected to the exercise assisting processing. In other words, the training dataset 323 may include a training data record 3234 including motion information 3231 generated independently of the exercise assisting processing (for example, generated for the training processing).

As an example, when the exercise assisting apparatus 3 assists a target person who does an exercise for rehabilitation (that is, a patient), at least one training data record 3234 may include motion information 3231 indicating motions of the patient. On the other hand, at least one training data record 3234 may include motion information 3231 indicating motions of a person who is different from the patient and does the exercise for rehabilitation. For example, at least one training data record 3234 may include motion information 3231 indicating motions of a healthcare worker who is demonstrating exemplary motions for bringing about an effect of rehabilitation.

Note that in the following description, for explanatory convenience, a person who does motions indicated by motion information 3231 is referred to as "sample person". Sample persons may include an arbitrary person who is not subjected to the exercise assisting processing, and may include a target person who is subjected to the exercise assisting processing.

As described above, motion information 3211 indicating motions of a target person is stored in the motion information DB 321. In such a case, the motion information 3211 stored in the motion information DB 321 may be used also for motion information 3231 in the training dataset 323. In such a case, the training dataset 323 does not necessarily need to include motion information 3231 (particularly, motion information 3231 indicating motions of a target person).

The ground truth label 3232 is a label (in other words, an information tag) indicating a correct answer for a result of inferring motions of a sample person indicated by the motion information 3211 corresponding to the ground truth label 3232. In other words, the ground truth label 3232 is a label indicating a correct answer for an inference result that is outputted by the inference model 322 when the motion information 3211 corresponding to the ground truth label 3232 is inputted into the inference model 322.

Annotation of assigning a ground truth label 3232 to motion information 3231 may be manually performed by a person who checks motions of a sample person. Persons who check motions of a sample person may include a person who has expertise for discriminating between exemplary motions and non-exemplary motions and identifying a reason why it is determined that the non-exemplary motions are not exemplary. Persons who check motions of a sample person may include a person who does not have expertise for discriminating between exemplary motions and non-exemplary motions and/or identifying a reason why it is determined that the non-exemplary motions are not exemplary, but is capable of discriminating between exemplary motions and non-exemplary motions and identifying a reason why it is determined that the non-exemplary motions are not exemplary, according to clearly stated rules. Alternatively, the annotation of assigning a ground truth label 3232 to motion information 3231, in addition to, or instead of, being manually performed by a person who checks motions of a sample person, may be performed by an apparatus capable of automatically assigning a ground truth label 3232, based on motion information 3231.

The training dataset 323 may be generated by the exercise assisting apparatus 3. In such a case, the exercise assisting apparatus 3 may generate the training dataset 323 by generating distance images by picking up images of a sample person by using the distance image collection apparatus 2, generating motion information 3231 from the distance images, and assigning a ground truth label 3232 to the motion information 3231. Alternatively, the training dataset 323 may be generated by an external apparatus that is different from the exercise assisting apparatus 3, in addition to, or instead of, the exercise assisting apparatus 3.

The exercise assisting apparatus 3 may perform additional training processing as the training processing, in addition to, or instead of, the pre-training processing. The additional training processing is training processing performed by using newly acquired motion information 3231 after the pre-training processing is performed. The additional training processing is training processing that is performed by using second motion information 3231 that is different from first motion information 3231, under a situation where training processing (for example, the pre-training processing or other already-performed additional training processing; the same holds true hereinafter) has been already performed by using the first motion information 3231.

The additional training processing may include training processing that is performed by using motion information 3231 indicating motions of a sample person doing a second type of exercise that is different from a first type of exercise, under a situation where training processing has been already performed by using motion information 3231 indicating motions of the sample person doing the first type of exercise. In other words, the additional training processing may include training processing that is performed by using motion information 3231 indicating motions of a sample person doing a different type of exercise from an exercise learned through training processing performed in the past (that is, an exercise unknown to the inference model 322). As an example, the additional training processing may include training processing that is performed by using motion information 3231 indicating motions of a sample person doing a lunge that is different from a squat, under a situation where training processing has been already performed by using motion information 3231 indicating motions of the sample person doing a squat.

The additional training processing may include training processing that is performed by using motion information 3231 indicating second exemplary motions for a certain exercise, under a situation where training processing has been already performed by using the training dataset 323 including motion information 3231 indicating first exemplary motions for the same exercise. In other words, the additional training processing may include training processing that is performed by using motion information 3231 indicating second exemplary motions that are different from first exemplary motions learned through training processing performed in the past (that is, exemplary motions unknown to the inference model 322). As an example, exemplary motions can vary according to a purpose of doing an exercise. For example, exemplary motions in a case where a target person does squats for rehabilitation in a late phase of recovery might be different from exemplary motions in a case where the same target person does squats for rehabilitation in an early phase of recovery. In such a case, the additional training processing may include training processing that is performed by using motion information 3231 indicating the exemplary motions for a squat for rehabilitation in the late phase of recovery, under a situation where training processing has been already performed by using motion information 3231 indicating the exemplary motions for a squat for rehabilitation in the early phase of recovery. As another example, exemplary motions can vary according to a target person who does an exercise. For example, exemplary motions in a case where a target person who has suffered a stroke does squats for rehabilitation might be different from exemplary motions in a case where a target person who has sustained a leg fracture does squats for rehabilitation. In such a case, the additional training processing may include training processing that is performed by using motion information 3231 indicating the exemplary motions in the case where the target person who has suffered a stroke does squats for rehabilitation, under a situation where training processing has been already performed by using motion information 3231 indicating the exemplary motions in the case where the target person who has sustained a leg fracture does squats for rehabilitation.

Note that the additional training processing may be regarded as processing of updating the inference model 322 already generated through the pre-training processing or other already-performed additional training processing. The processing of updating the inference model 322 already generated through the pre-training processing or other already-performed additional training processing may be regarded as processing of generating a new inference model 322 from the inference model 322 already generated through the pre-training processing or other already-performed additional training processing (that is, the inference model 322 trained beforehand). Note that the inference model 322 already generated through the pre-training processing or other already-performed additional training processing may be referred to as "pre-trained model". The inference model 322 already generated through the pre-training processing or other already-performed additional training processing may be regarded as one specific example of a "pre-trained model" in additional statements, which will be described later.

FIG. 2 shows an example of the logical functional block implemented in the computation apparatus 31 in order to perform the training processing including the pre-training processing and the additional training processing. As shown in FIG. 2, a model generation unit 314 is implemented in the computation apparatus 31. Note that operation of the model generation unit 314 will be described in detail later, and a description thereof is therefore omitted here.

The storage apparatus 32 is capable of storing desired data. For example, the storage apparatus 32 may temporarily store the computer program that is executed by the computation apparatus 31. The storage apparatus 32 may temporarily store data that is temporarily used by the computation apparatus 31 when the computation apparatus 31 executes the computer program. The storage apparatus 32 may store data that is kept by the exercise assisting apparatus 3 on a long-term basis. Note that the storage apparatus 32 may include at least one of a RAM (Random Access Memory), a ROM (Read Only Memory), a hard disk apparatus, a magneto-optical disk apparatus, an SSD (Solid State Drive), and a disk array apparatus. In other words, the storage apparatus 32 may include a non-transitory recording medium.

In the present example embodiment, the storage apparatus 32 may store the motion information DB 321, the inference model 322, and the training dataset 323 described above. Further, the storage apparatus 32 may store a person information DB 324 that stores information related to a target person.

The communication apparatus 33 is capable of communicating with an external apparatus outside of the exercise assisting apparatus 3 through an undepicted communication network. For example, when the exercise assisting apparatus 3 and the color image collection apparatus 1 are connected through the communication network, the communication apparatus 33 may receive a color image from the color image collection apparatus 1. For example, when the exercise assisting apparatus 3 and the distance image collection apparatus 2 are connected through the communication network, the communication apparatus 33 may receive a distance image from the distance image collection apparatus 2.

The input apparatus 34 is an apparatus that receives information as an input to the exercise assisting apparatus 3 from an outside of the exercise assisting apparatus 3. For example, the input apparatus 34 may include an operation apparatus (for example, at least one of a keyboard, a mouse, and a touch panel) that is operable by a patient. For example, the input apparatus 34 may include a recording medium reading apparatus capable of reading the information recorded as data in a recording medium that is externally attachable to the exercise assisting apparatus 3.

The output apparatus 35 is an apparatus that outputs information to the outside of the exercise assisting apparatus 3. For example, the output apparatus 35 may output the information as an image. In other words, the output apparatus 35 may include a display apparatus (so-called display) capable of displaying an image indicating the information desired to be outputted. For example, the output apparatus 35 may output the information as voice. In other words, the output apparatus 35 may include an audio apparatus (so-called speaker) capable of outputting voice. For example, the output apparatus 35 may output the information on a sheet of paper. In other words, the output apparatus 35 may include a printing apparatus (so-called printer) capable of printing the desired information on a sheet of paper. Note that in the following description, for simplicity of description, an example is described in which the output apparatus 35 is a display apparatus.

(2) Exercise Assisting Processing Performed by Exercise Assisting Apparatus 3

Next, processing performed by the exercise assisting apparatus 3 is described. As described above, the exercise assisting apparatus 3 may perform the exercise assisting processing. Further, the exercise assisting apparatus 3 may perform the training processing (specifically, at least one of the pre-training processing and the additional training processing) for training the inference model 322 that is used in the exercise assisting processing. Accordingly, in the following, the pre-training processing, the additional training processing, and the exercise assisting processing are described sequentially.

(2-1) Pre-Training Processing

First, the pre-training processing is described with reference to FIG. 9. FIG. 9 is a flowchart showing a flow of the pre-training processing.

As shown in FIG. 9, the model generation unit 314 acquires the training dataset 323 (step S11). For example, when the training dataset 323 is stored in the storage apparatus 32, the model generation unit 314 may acquire the training dataset 323 from the storage apparatus 32. For example, when the training dataset 323 is stored in a recording medium that is externally attachable to the exercise assisting apparatus 3, the model generation unit 314 may acquire the training dataset 323 from the recording medium by using the recording medium reading apparatus (for example, the input apparatus 34) included in the exercise assisting apparatus 3. For example, when the training dataset 323 is stored in an external apparatus (for example, a server) outside of the exercise assisting apparatus 3, the model generation unit 314 may acquire the training dataset 323 from the external apparatus by using the communication apparatus 33.

Thereafter, the element division unit 312 divides each of a plurality of pieces of motion information 3231 included in the training dataset 323 acquired in step S11, into a plurality of pieces of motion element information 3235 (step S12). Note that the processing of dividing motion information 3231 into a plurality of pieces of motion element information 3235 in the training processing may be the same as the processing of dividing motion information 3211 into a plurality of pieces of motion element information 3214 in the above-described exercise assisting processing. In other words, the element division unit 312 divides each piece of motion information 3231 into a plurality of pieces of motion element information 3235, according to regularity (in other words, periodicity) in motions of a sample person. As a result, as many motion element datasets, each of which includes a plurality of pieces of motion element information 3235 generated from one piece of motion information 3231, as the number of the pieces of motion information 3231 included in the training dataset 323 acquired in step S11 are generated.

Thereafter, the model generation unit 314 performs machine learning for generating the inference model 322, by using the plurality of pieces of motion element information 3235 (the plurality of motion element datasets) generated in step S12 (step S13). Specifically, the model generation unit 314 inputs a motion element dataset (that is, a plurality of pieces of motion element information 3235) into the inference model 322 before the machine learning is performed (that is, the inference model 322 in an initial state or a default state). As a result, the inference model 322 outputs an inference result corresponding to the motion element dataset. The model generation unit 314 iterates the similar operation as many times as the number of the motion element datasets. Thereafter, the model generation unit 314 updates a parameter of the inference model 322 based on the machine learning in such a manner as to decrease (preferably, minimize) a loss function based on an error between each inference result outputted by the inference model 322 and each corresponding ground truth label 3232 included in the training dataset 323 acquired in step S11. As a result, the inference model 322 is generated that has learned motions indicated by each piece of motion information 3231 included in the training dataset 323. In other words, the inference model 322 is generated that has learned antecedent dependency of the plurality of pieces of motion element information 3235 generated by dividing each piece of motion information 3231 included in the training dataset 323.

Note that in addition to, or instead of, inputting the plurality of pieces of motion element information 3235 into the inference model 322, the model generation unit 314 may extract features of the plurality of pieces of motion element information 3235 and input the extracted features into the inference model 322.

Thereafter, the model generation unit 314 may store the inference model 322 generated in step S13 in the storage apparatus 32 (step S14). The inference model 322 stored in the storage apparatus 32 may be used for the exercise assisting processing. The inference model 322 stored in the storage apparatus 32 may be used for the additional training processing.

(2-2) Additional Training Processing

Figure 10:
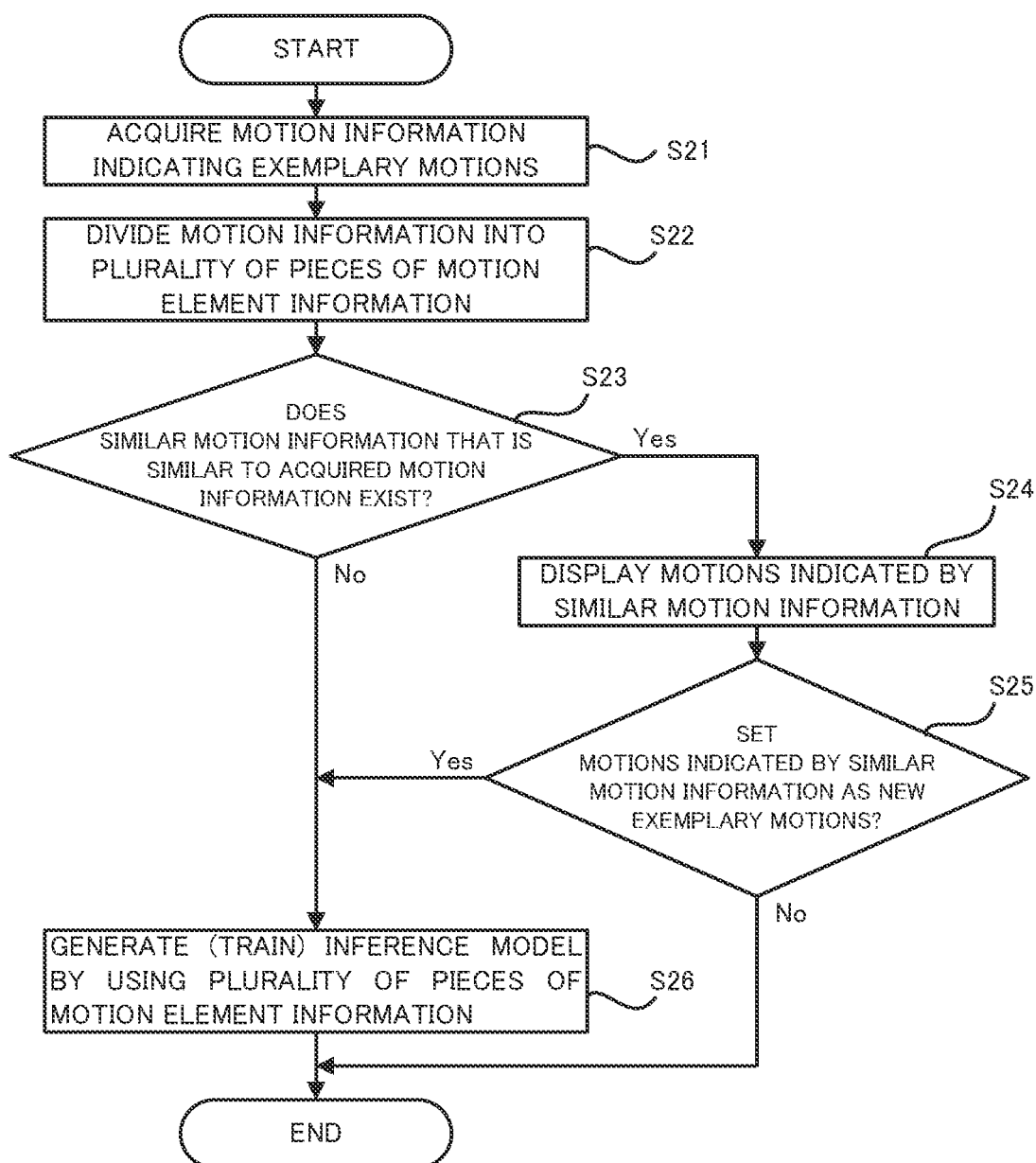
FIG. 10 is a flowchart showing a flow of additional training processing.

Next, the additional training processing is described with reference to FIG. 10. FIG. 10 is a flowchart showing a flow of the pre-training processing.

As shown in FIG. 10, the model generation unit 314 acquires motion information 3231 that is used to perform the additional training processing (step S21). For example, when the motion information 3231 is stored in the storage apparatus 32, the model generation unit 314 may acquire the motion information 3231 from the storage apparatus 32. For example, when the motion information 3231 is stored in a recording medium that is externally attachable to the exercise assisting apparatus 3, the model generation unit 314 may acquire the motion information 3231 from the recording medium by using the recording medium reading apparatus (for example, the input apparatus 34) included in the exercise assisting apparatus 3. For example, when the motion information 3231 is stored in an external apparatus (for example, a server) outside of the exercise assisting apparatus 3, the model generation unit 314 may acquire the motion information 3231 from the external apparatus by using the communication apparatus 33. When the distance image collection apparatus 2 generates new distance images by picking up new images of a sample person, the motion information generation unit 311 may generate new motion information 3231 based on the new distance images generated, and the model generation unit 314 may acquire the new motion information 3231 generated by the motion information generation unit 311.

The additional training processing may include training processing that is performed by using motion information 3231 indicating motions of a sample person doing a second type of exercise that is different from a first type of exercise learned through training processing performed in the past (that is, an exercise unknown to the inference model 322), as described above. Accordingly, in step S21, the model generation unit 314 may acquire motion information 3231 indicating motions of a sample person doing a different type of exercise from an exercise already learned by the inference model 322 through training processing performed in the past. Particularly, the model generation unit 314 may acquire motion information 3231 indicating exemplary motions of the sample person doing the different type of exercise from the exercise already learned by the inference model 322 through the training processing performed in the past.

The additional training processing may include training processing that is performed by using motion information 3231 indicating second exemplary motions that are different from first exemplary motions learned through training processing performed in the past, as described above. Accordingly, in step S21, the model generation unit 314 may acquire motion information 3231 indicating second exemplary motions that are different from first exemplary motions already learned by the inference model 322 through training processing performed in the past.

In any case, in the additional training processing, it is preferable that the model generation unit 314 acquire motion information 3231 indicating exemplary motions for a certain exercise. Note that "exemplary motions" here may refer to motions that are exemplary to a target person assisted through the exercise assisting processing. As described above, motions that are exemplary to a target person can vary according to the target person's purpose of doing an exercise. Motions that are exemplary to a target person can vary also according to the target person. Accordingly, the model generation unit 314 may acquire motion information 3231 indicating motions that are exemplary to a target person, depending on each individual case.

Note that when information related to a sample person who is doing the motions indicated by the motion information 3231 acquired in step S21 is stored in the person information DB 324, the model generation unit 314 may also acquire the information related to the sample person who is doing the motions indicated by the motion information 3231 acquired in step S21.

Thereafter, the element division unit 312 divides the motion information 3231 acquired in step S21 into a plurality of pieces of motion element information 3235 (step S22). Note that the processing in step S22 may be the same as the above-described processing in step S12 in FIG. 9.

Thereafter, in parallel with, or immediately before or after, the processing in step S22, the model generation unit 314 determines whether or not there exists, as motion information 3231 already learned by the inference model 322 through the training processing performed in the past, motion information 3231 that is similar to (or the same as) (hereinafter, referred to as "similar motion information 3231") the motion information 3231 acquired in step S21 (step S23). In other words, the model generation unit 314 determines whether or not similar motion information 3231 indicating motions that are similar to (or the same as) the motions indicated by the motion information 3231 acquired in step S21 is included among motion information 3231 already learned by the inference model 322 through the training processing performed in the past.

The motion information 3231 used in the training processing (that is, the motion information 3231 already learned by the inference model 322) has been already plotted, as a vector representing the motion information, in the presentation space defined by the inference model 322. Accordingly, the model generation unit 314 may determine whether or not similar motion information 3231 exists as motion information 3231 already learned by the inference model 322, by determining whether or not a vector representing the motion information 3231 acquired in step S21 has been already plotted in the presentation space defined by the inference model 322.

When it is determined, as a result of the determination in step S23, that similar motion information 3231 does not exist (step S23: No), it is presumed that the motions indicated by the motion information 3231 acquired in step S21 show exemplary motions that have not yet been learned by the inference model 322. In such a case, the model generation unit 314 performs machine learning for generating (here, updating or retraining) the inference model 322 by using the plurality of pieces of motion element information 3235 generated in step S22 (step S26). Note that the processing in step S23 may be the same as the above-described processing in step S13 in FIG. 9. As a result, the motion information 3231 that has not yet been learned by the inference model 322 through the training processing performed in the past is newly learned by the inference model 322.

As described above, in the additional training processing, machine learning using motion information 3231 indicating new exemplary motions is performed. On the other hand, in the additional training processing, machine learning using motion information 3231 indicating different motions from the new exemplary motions (that is, motions displaced from the new exemplary motions) does not necessarily need to be performed.

When it is determined, as a result of the determination in step S23, that similar motion information 3231 exists (step S23: No), it is likely that the motions indicated by the motion information 3231 acquired in step S21 have been already learned by the inference model 322 through the training processing performed in the past. In such a case, the model generation unit 314 controls the output apparatus 35 that is a display apparatus in such a manner that the output apparatus 35 displays the motions indicated by the motion information 3231 acquired in step S21 (step S24). In other words, the model generation unit 314 controls the output apparatus 35 that is a display apparatus in such a manner that the output apparatus 35 displays the sample person who is doing the motions indicated by the motion information 3231 acquired in step S21 (step S24). For example, the model generation unit 314 may control the output apparatus 35 that is a display apparatus in such a manner that the output apparatus 35 displays color images generated by the color image collection apparatus 1 picking up images of the sample person. As a result, an operator of the exercise assisting apparatus 3 can check the motions indicated by the motion information 3231 acquired in step S21.

Thereafter, the model generation unit 314 determines whether or not to set the motions indicated by the motion information 3231 acquired in step S21, as new exemplary motions (step S25). For example, the model generation unit 314 may determine whether or not to set the motions indicated by the motion information 3231 acquired in step S21 as new exemplary motions, based on an instruction from the operator of the exercise assisting apparatus 3 who has checked the motions indicated by the motion information 3231 acquired in step S21.

When it is determined, as a result of the determination in step S25, that the motions indicated by the motion information 3231 acquired in step S21 are set as new exemplary motions (step S25: Yes), the model generation unit 314 performs machine learning for generating (here, updating or retraining) the inference model 322 by using the plurality of pieces of motion element information 3235 generated in step S22 (step S26). When it is determined, as a result of the determination in step S25, that the motions indicated by the motion information 3231 acquired in step S21 are not set as new exemplary motions (step S25: No), the model generation unit 314 does not need to perform the processing in step S26.

However, in the additional training processing, the exercise assisting apparatus 3 may omit to perform the processing in steps S23 to S25. In other words, the exercise assisting apparatus 3 may perform machine learning for generating (here, updating or retraining) the inference model 322 by using the plurality of pieces of motion element information 3235 generated in step S22, without determining whether or not similar motion information 3231 exists.

(2-3) Exercise Assisting Processing

Figure 11:
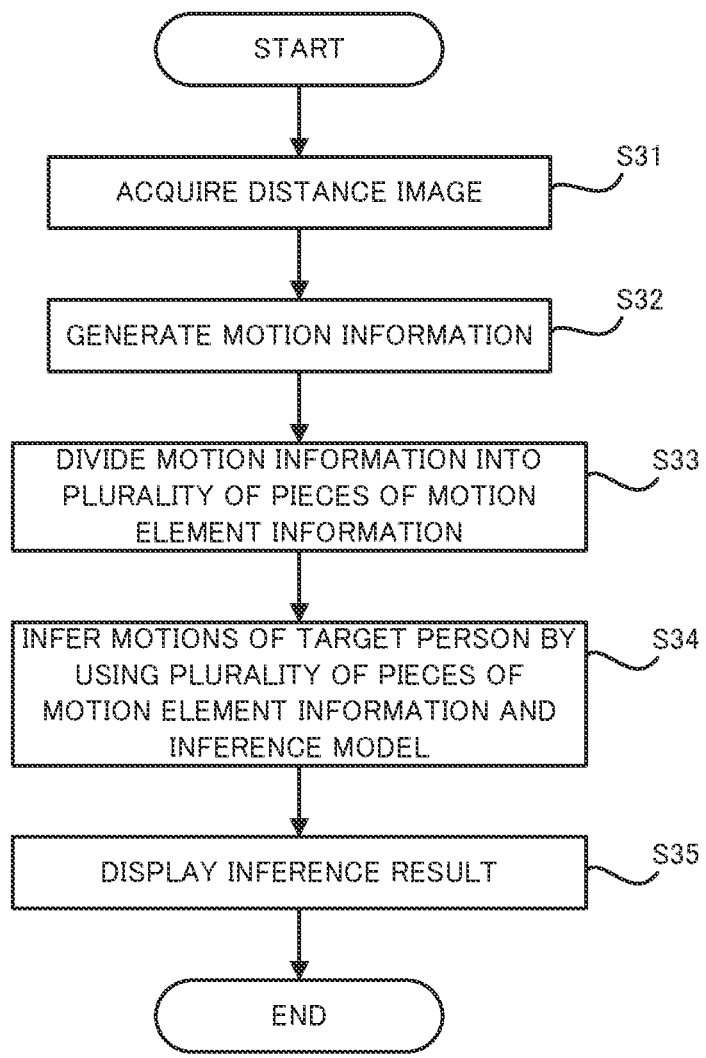
FIG. 11 is a flowchart showing a flow of exercise assisting processing.

Next, the exercise assisting processing is described with reference to FIG. 11. FIG. 11 is a flowchart showing a flow of the exercise assisting processing.

As shown in FIG. 11, the motion information generation unit 311 acquires distance images in which a target person appears (step S31). Specifically, when the exercise assisting processing is performed, a target person who is subjected to the exercise assisting processing is doing an exercise within an image pickup range of the distance image collection apparatus 2. Accordingly, the distance image collection apparatus 2 generates the distance images by picking up images of the target person doing the exercise. The motion information generation unit 311 acquires the distance images generated by the distance image collection apparatus 2. Note that the color image collection apparatus 1 also generates color images by picking up images of the target person doing the exercise.

Thereafter, the motion information generation unit 311 generates motion information 3211 by using the distance images acquired in step S31 (step S32). Thereafter, the element division unit 312 divides the motion information 3211 generated in step S32 into a plurality of pieces of motion element information 3214 (step S33).

Thereafter, the motion inference unit 313 infers motions of the target person by using the plurality of pieces of motion element information 3214 generated in step S33 and the inference model 322 generated through the above-described training processing (step S34). Specifically, the motion inference unit 313 acquires the inference model 322 stored in the storage apparatus 32. Alternatively, when the inference model 322 is stored in a recording medium that is externally attachable to the exercise assisting apparatus 3, the motion inference unit 313 may acquire the inference model 322 from the recording medium by using the recording medium reading apparatus (for example, the input apparatus 34) included in the exercise assisting apparatus 3. For example, when the inference model 322 is stored in an external apparatus (for example, a server) outside of the exercise assisting apparatus 3, the motion inference unit 313 may acquire the inference model 322 from the external apparatus by using the communication apparatus 33. Thereafter, the motion inference unit 313 inputs the plurality of pieces of motion element information 3214 generated in step S33, into the inference model 322 generated through the training processing. As a result, the inference model 322 outputs a result of inferring the motions of the target person. For example, the inference model 322 may output a result of inferring whether or not the motions of the target person are exemplary motions. For example, the inference model 322 may output a result of inferring a difference (that is, a displacement) between the motions of the target person and the exemplary motions.

Note that in step S34, in addition to, or instead of, inputting the plurality of pieces of motion element information 3214 into the inference model 322, the motion inference unit 313 may extract features of the plurality of pieces of motion element information 3214 and input the extracted features into the inference model 322. Moreover, Thereafter, the motion inference unit 313 controls the output apparatus 35 that is a display apparatus in such a manner that the output apparatus 35 displays the result of inferring the motions of the target person in step S34 (step S35). However, the motion inference unit 313 does not need to control the output apparatus 35 that is a display apparatus in such a manner that the output apparatus 35 displays the result of inferring the motions of the target person in step S34.

For example, the motion inference unit 313 may control the output apparatus 35 in such a manner that the output apparatus 35 displays the result of inferring whether or not the motions of the target person are exemplary motions. As a result, the target person can recognize whether or not the motions of the target person are the exemplary motions, by checking the inference result displayed on the output apparatus 35. In such a case, the target person can correct the motions of the target person in such a manner that the motions of the target person approximate or match the exemplary motions. For example, the motion inference unit 313 may control the output apparatus 35 in such a manner that the output apparatus 35 displays the result of inferring a difference (that is, a displacement) between the motions of the target person and the exemplary motions. As a result, the target person can recognize the difference between the motions of the target person and the exemplary motions, by checking the inference result displayed on the output apparatus 35. In such a case, the target person can correct the motions of the target person in such a manner that the motions of the target person approximate or match the exemplary motions (typically, correct the motions in such a manner as to eliminate the displayed difference).

Figure 12:
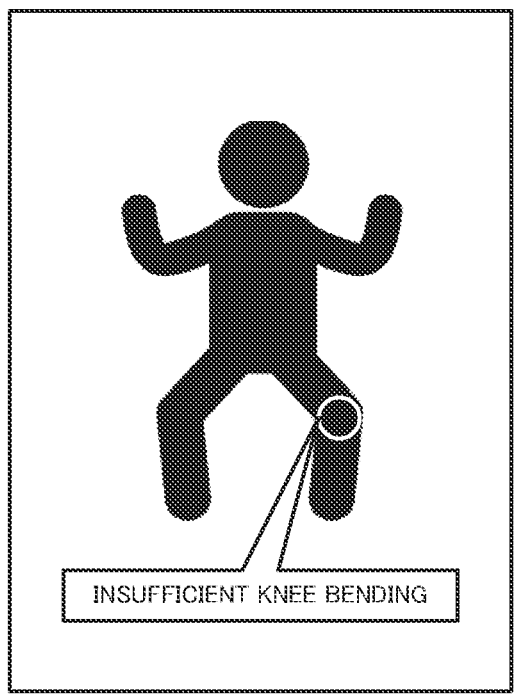
FIG. 12 shows an output example (presentation example) of a result of inferring motions of a target person in the exercise assisting processing.

The motion inference unit 313 may control the output apparatus 35 in such a manner that the output apparatus 35 displays the result of inferring the motions of the target person, together with a color image generated by the color image collection apparatus 1 picking up an image of the target person. In such a case, when it is inferred in step S34 that the motions of the target person are not the exemplary motions, the motion inference unit 313 may cause notification information for notifying the target person of a body part of the target person that is displaced (that is, deviates) from the exemplary motions to be displayed, in a superimposed manner, on the color image in which the target person appears who is doing the motions displaced from the exemplary motions. For example, when it is inferred that the motions of the target person doing squats, which are an example of the exercise, are not the exemplary motions because the knees of the target person are less bent, the motion inference unit 313 may cause notification information for notifying the target person that the knees of the target person are less bent to be displayed, in a superimposed manner, on the color image, as shown in FIG. 12. In the example shown in FIG. 12, the notification information includes a display object indicating the knees of the target person and a text message indicating that the knees of the target person are less bent. As a result, the target person can intuitively recognize the difference between the motions of the target person and the exemplary motions. Accordingly, the target person can intuitively correct the motions of the target person in such a manner that the motions of the target person approximate or match the exemplary motions (typically, correct the motions in such a manner as to eliminate the displayed difference).

(3) Specific Examples of Scenario to which Exercise Assisting System SYS is Applied Next, specific examples of a scenario to which the exercise assisting system SYS is applied are described. Note that the scenario to which the exercise assisting system SYS is applied is not limited to the specific examples described below.

(3-1) First Specific Example

In a first specific example, the exercise assisting system SYS is applied to a scenario in which, for example, a patient who is half-paralyzed due to a stroke does squats as an exercise for rehabilitation. In such a case, for example, the pre-training processing may be performed by using motion information 3231 indicating motions of a healthcare worker doing a squat in a laboratory (that is, exemplary motions), and motion information 3231 indicating motions of an arbitrary elderly person doing a squat in the laboratory (that is, different motions from the exemplary motions). Thereafter, the additional training processing may be performed by using motion information 3231 generated by the patient who is subjected to the exercise assisting processing (that is, the patient who is half-paralyzed due to a stroke) actually doing squats in a hospital (that is, motion information 3231 indicating exemplary motions specific to the half-paralyzed patient). As a result, in the exercise assisting processing, the exercise assisting apparatus 3 can infer a difference between motions of the patient (that is, the patient half-paralyzed due to a stroke) doing squats for rehabilitation in the hospital and the exemplary motions.

(3-2) Second Specific Example

In a second specific example, the exercise assisting system SYS is applied to a scenario in which, for example, an elderly person does physical exercise as an exercise for care prevention. In such a case, for example, the pre-training processing may be performed by using motion information 3231 indicating motions of a healthcare worker doing physical exercise in a laboratory (that is, exemplary motions), and motion information 3231 indicating motions of an arbitrary elderly person doing physical exercise in the laboratory (that is, different motions from the exemplary motions). Thereafter, the additional training processing may be performed by using motion information 3231 generated by the elderly person who is subjected to the exercise assisting processing actually doing physical exercise in a local meeting place that is, motion information 3231 indicating (exemplary motions specific to the elderly person who is subjected to the exercise assisting processing). As a result, in the exercise assisting processing, the exercise assisting apparatus 3 can infer a difference between motions of the elderly person doing the exercise for care prevention in the local meeting place and the exemplary motions.

(3-3) Third Specific Example

In a third specific example, the exercise assisting system SYS is applied to a scenario in which, for example, an elderly person does a TUG (Timed Up and Go) test as an exercise for care prevention. In such a case, for example, the pre-training processing may be performed by using motion information 3231 indicating motions of a healthcare worker doing a different exercise from the TUG test in a laboratory (in other words, exemplary motions for the different exercise from the TUG test), and motion information 3231 indicating motions of an arbitrary elderly person doing the different exercise from the TUG test in the laboratory (that is, different motions from the exemplary motions for the different exercise from the TUG test). Thereafter, the additional training processing may be performed by using motion information 3231 generated by a healthy person without concern about care actually doing the TUG test that is, motion information 3231 indicating (exemplary motions specific to the TUG test). As a result, in the exercise assisting processing, the exercise assisting apparatus 3 can infer a difference between motions of the elderly person doing the TUG test for care prevention in a facility for elderly people to stay, and the exemplary motions for the TUG test.

(3-4) Fourth Specific Example

In a fourth specific example, the exercise assisting system SYS is applied to a scenario in which, for example, a member of a workout facility does squats as an exercise to get in shape. In such a case, for example, the pre-training processing may be performed by using motion information 3231 indicating exemplary motions of a trainer doing a lunge that is different from a squat in the workout facility, and motion information 3231 indicating different motions from the exemplary motions of the trainer doing a lunge that is different from a squat in the workout facility. Thereafter, the additional training processing may be performed by using motion information 3231 generated by the trainer doing a squat in the workout facility that is, motion information 3231 indicating (exemplary motions specific to the squat). As a result, in the exercise assisting processing, the exercise assisting apparatus 3 can infer a difference between motions of the member doing squats in the workout system and the exemplary motions for a squat.

(3-5) Fifth Specific Example

In a fifth specific example, the exercise assisting system SYS is applied to a scenario in which, for example, an amateur athlete involved in a sport does pitching practice as an exercise. In such a case, for example, the pre-training processing may be performed by using motion information 3231 indicating motions of a professional athlete doing overhand or sidearm pitching practice in a laboratory (that is, overhand or sidearm exemplary motions), and motion information 3231 indicating motions of an amateur athlete doing overhand or sidearm pitching practice in the laboratory (that is, different motions from the exemplary motions). Thereafter, the additional training processing may be performed by using motion information 3231 generated by the professional athlete doing three-quarters pitching practice in an outdoor practice field that is, motion information 3231 indicating (exemplary motions specific to three quarters). As a result, in the exercise assisting processing, the exercise assisting apparatus 3 can infer a difference between motions of the amateur athlete doing three-quarters pitching practice in the outdoor practice field, and the exemplary motions for three quarters.

(4) Technical Effects of Exercise Assisting System SYS

As described above, in the present example embodiment, the exercise assisting apparatus 3 is capable of generating the inference model 322 by performing the training processing. The exercise assisting apparatus 3, in particular, generates a plurality of pieces of motion element information 3235 by dividing, along a time series, motion information 3231 indicating motions of a sample person, according to regularity in the motion information 3231, and performs the training processing using the plurality of pieces of motion element information 3235, thereby generating the inference model 322 (for example, the model using Bert as described above) capable of inferring motions of a target person based on antecedent dependency of a plurality of pieces of motion element information 3214. Accordingly, the exercise assisting apparatus 3 is capable of performing the training processing of causing the inference model 322 to learn antecedent dependency of the plurality of pieces of motion element information 3235. In other words, when generating the inference model 322, the exercise assisting apparatus 3 can take into consideration antecedent dependency of the plurality of pieces of motion element information 3235. To put it another way, when generating the inference model 322, the exercise assisting apparatus 3 can take into consideration a flow of changes in motion of the sample person. As a result, since the exercise assisting apparatus 3 infers the motions of the target person by using the inference model 322 that is generated with the flow of changes in motion of the sample person taken into consideration, the exercise assisting apparatus 3 can take into consideration antecedent dependency of the plurality of pieces of motion element information 3214 when inferring the motions of the target person. In other words, when inferring the motions of the target person, the exercise assisting apparatus 3 can take into consideration a flow of changes in motion of the target person. As a result, when inferring the motions of the target person, the exercise assisting apparatus 3 can infer the motions of the target person more appropriately (for example, with higher accuracy), as compared to an exercise assisting apparatus in a comparison example that does not take into consideration a flow of changes in motion of a target person.

Moreover, in the present example embodiment, the additional training processing is performed in addition to the pre-training processing. In the additional training processing in particular, motion information 3231 indicating new exemplary motions that have not been learned by the inference model 322 in the training processing performed in the past are learned by the inference model 322. On the other hand, in the additional training processing, motion information 3231 indicating different motions from the new exemplary motions (that is, motions displaced from the new exemplary motions) does not need to be newly learned by the inference model 322. Also in such a case, since machine learning is performed through the training processing performed in the past (for example, the pre-training processing) by using motion information 3231 indicating another exemplary motions that are different from the new exemplary motions, and motion information 3231 indicating motions displaced from the another exemplary motions, the inference model 322 updated through the additional training processing can output an inference result obtained by inferring whether motions of a target person are the new exemplary motions, or are different motions from the new exemplary motions.

As an example, the additional training processing may be performed by using motion information 3231 indicating exemplary motions of a sample person doing a second type of exercise that is different from a first type of exercise already learned by the inference model 322 through the training processing performed in the past, as described above. In such a case, in the additional training processing, while the motion information 3231 indicating the exemplary motions for the second type of exercise is learned by the inference model 322, motion information 3231 indicating motions displaced from the exemplary motions for the second type of exercise does not need to be newly learned by the inference model 322. Also in such a case, the inference model 322 has learned, through the training processing performed in the past, both exemplary motions for the first type of exercise and different motions from the exemplary motions for the first type of exercise. As a result, the inference model 322 can output an inference result obtained by inferring whether motions of a target person doing the second type of exercise are the exemplary motions for the second type of exercise, or are different motions from the exemplary motions for the second type of exercise.

More specifically, a scenario is described in which the additional training processing is performed by using motion information 3231 indicating exemplary motions for a lunge, under a situation where the pre-training processing has been performed by using motion information 3231 indicating exemplary motions for a squat and different motions from the exemplary motions for a squat. In such a case, in the additional training processing, while the motion information 3231 indicating the exemplary motions for a lunge is learned by the inference model 322, motion information 3231 indicating motions displaced from the exemplary motions for a lunge does not need to be newly learned by the inference model 322. Also in such a case, the inference model 322 has learned, through the training processing performed in the past, both the exemplary motions for a squat and the different motions from the exemplary motions for a squat. As a result, the inference model 322 can output an inference result obtained by inferring whether motions of a target person doing lunges are the exemplary motions for a lunge, or are different motions from the exemplary motions for a lunge.

As another example, under a situation where first exemplary motions for a certain exercise have been learned through the training processing performed in the past, the additional training processing may be performed by using motion information 3231 indicating second exemplary motions for the same exercise (note that the second exemplary motions are different from the first exemplary motions), as described above. In such a case, in the additional training processing, while the motion information 3231 indicating the second exemplary motions is learned by the inference model 322, motion information 3231 indicating motions displaced from the second exemplary motions does not need to be newly learned by the inference model 322. Also in such a case, the inference model 322 has learned, through the training processing performed in the past, both the first exemplary motions of a sample person doing the same exercise and the different motions from the first exemplary motions. As a result, the inference model 322 can output an inference result obtained by inferring whether motions of a target person doing the same exercise are the second exemplary motions, or are different motions from the second exemplary motions.

More specifically, a scenario is described in which the additional training processing is performed by using motion information 3231 indicating exemplary motions for a squat for rehabilitation in a late phase of recovery, under a situation where the pre-training processing has been performed by using motion information 3231 indicating exemplary motions for a squat for rehabilitation in an early phase of recovery and different motions from the exemplary motions for a squat for rehabilitation in the early phase of recovery. In such a case, in the additional training processing, while the motion information 3231 indicating the exemplary motions for a squat for rehabilitation in the late phase of recovery is learned by the inference model 322, motion information 3231 indicating motions displaced from the exemplary motions for a squat for rehabilitation in the late phase of recovery does not need to be newly learned by the inference model 322. Also in such a case, the inference model 322 has learned, through the training processing performed in the past, both the exemplary motions for a squat for rehabilitation in the early phase of recovery and the different motions from the exemplary motions for a squat for rehabilitation in the early phase of recovery. As a result, the inference model 322 can output an inference result obtained by inferring whether motions of a target person doing squats for rehabilitation in the late phase of recovery are the exemplary motions for a squat for rehabilitation in the late phase of recovery, or are different motions from the exemplary motions for a squat for rehabilitation in the late phase of recovery.

As described above, through the additional training processing, the inference model 322 is generated that is adapted to an exercise (particularly, exemplary motions for the exercise) done by a target person. The inference model 322 is generated that is adapted, in particular, to exemplary motions to a target person in each individual case. Accordingly, the target person can more appropriately recognize whether or not motions of the target person are the exemplary motions, as compared to a case where the additional training processing is not performed. Moreover, motion information 3231 indicating new exemplary motions that have not been learned by the inference model 322 through the training processing performed in the past does not necessarily need to be acquired in large quantities for the additional training processing. Accordingly, through the additional training processing, it is possible to relatively easily generate, from the inference model 322 already generated through the training processing performed in the past, the inference model 322 that is capable of inferring whether motions of a target person are the new exemplary motions, or are different motions from the new exemplary motions.

(5) Modifications

The exercise assisting apparatus 3 may generate a plurality of inference models 322. For example, the exercise assisting apparatus 3 may generate the plurality of inference models 322 for exercise categories, respectively. In other words, the exercise assisting apparatus 3 may generate separately an inference model 322 for inferring motions of a target person doing an exercise belonging to a first category, and an inference model 322 for inferring motions of a target person doing an exercise belonging to a second category that is different from the first category. In such a case, the exercise assisting apparatus 3 may perform the training processing using motion information 3231 indicating motions of a target person doing the exercise belonging to the first category, and the training processing using motion information 3231 indicating motions of a target person doing the exercise belonging to the second category independently.

The exercise categories may include a category based on a body part that is moved by an exercise. For example, the exercise assisting apparatus 3 may generate separately an inference model 322 for inferring motions of a target person doing an exercise mainly using an upper body, and an inference model 322 for inferring motions of a target person doing an exercise mainly using a lower body (for example, at least one of squats and lunges). For example, the exercise assisting apparatus 3 may generate separately an inference model 322 for inferring motions of a target person doing an exercise mainly using a right arm, and an inference model 322 for inferring motions of a target person doing an exercise mainly using a left arm.

The exercise categories may include a category based on a body part on which an exercise places an impact. For example, the exercise assisting apparatus 3 may generate separately an inference model 322 for inferring motions of a target person doing an exercise that places an impact mainly on an upper body, and an inference model 322 for inferring motions of a target person doing an exercise that places an impact mainly on a lower body. For example, the exercise assisting apparatus 3 may generate separately an inference model 322 for inferring motions of a target person doing an exercise that places an impact mainly on a right arm, and an inference model 322 for inferring motions of a target person doing an exercise that places an impact mainly on a left arm.

Figure 13:
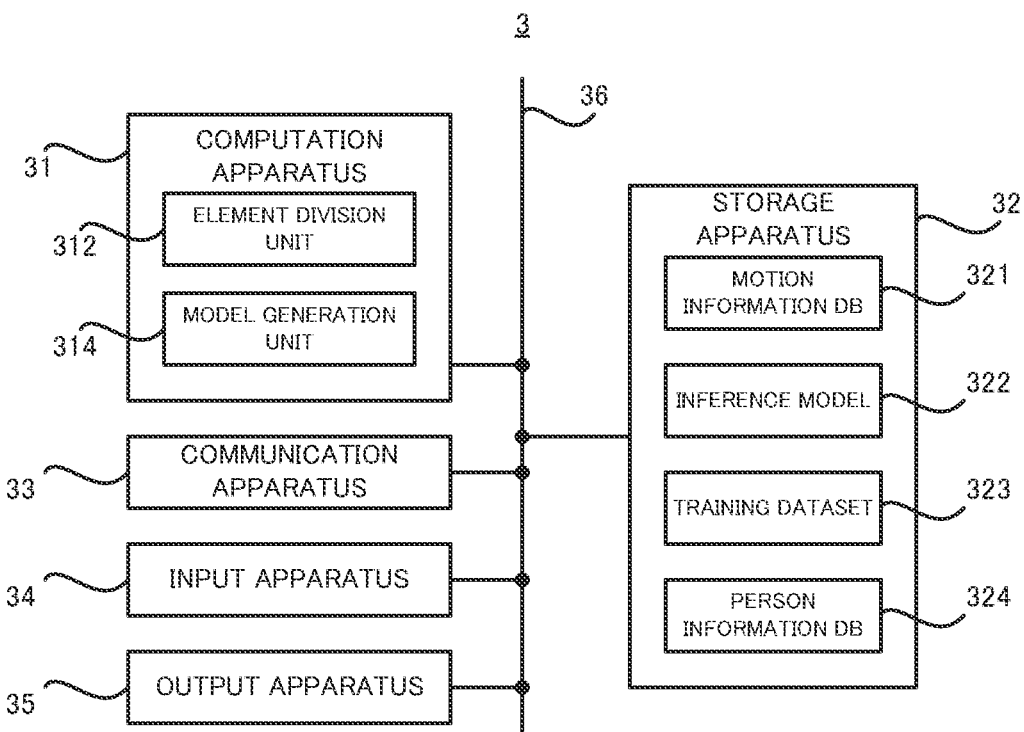
FIG. 13 is a block diagram showing a configuration of an exercise assisting apparatus in a modification.
Figure 14:
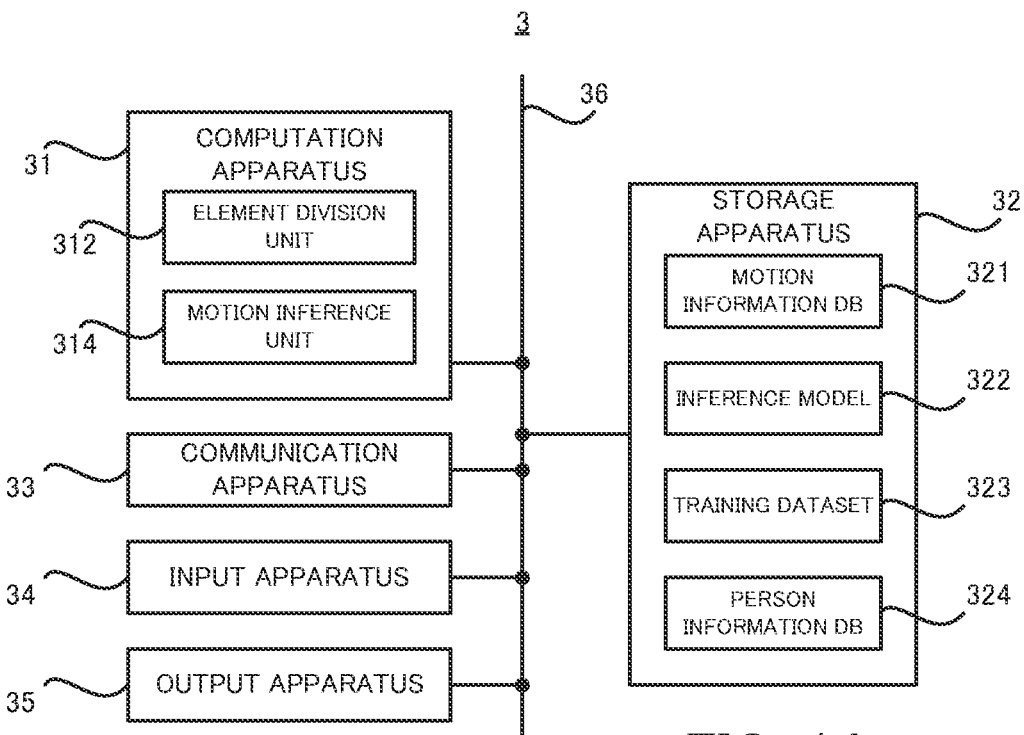
FIG. 14 is a block diagram showing a configuration of an exercise assisting apparatus in a modification.

In the above description, the exercise assisting apparatus 3 performs both the exercise assisting processing and the training processing. However, the exercise assisting apparatus 3 may perform any one of the exercise assisting processing and the training processing, while not needing to perform the other one of the exercise assisting processing and the training processing. When the exercise assisting apparatus 3 does not perform the exercise assisting processing, the exercise assisting apparatus 3 may omit to include the motion inference unit 313 as shown in FIG. 13. When the exercise assisting apparatus 3 does not perform the training processing, the exercise assisting apparatus 3 may omit to include the model generation unit 314 as shown in FIG. 14.

In the above description, the exercise assisting apparatus 3 (particularly, the element division unit 312) divides motion information 3211 into a plurality of pieces of motion element information 3214. However, the operator of the exercise assisting apparatus 3 may manually divide motion information 3211 into a plurality of pieces of motion element information 3214.

In the above description, the exercise assisting apparatus 3 generates motion information 3211, based on distance images generated by the distance image collection apparatus 2. However, the exercise assisting apparatus 3 may generate motion information 3211, based on an output of an apparatus that is different from the distance image collection apparatus 2. For example, the exercise assisting apparatus 3 may generate motion information 3211, based on an output (detection result) of a motion sensor capable of detecting motions of a target person or a sample person by detecting markers worn by the target person or the sample person. For example, the exercise assisting apparatus 3 may generate motion information 3211, based on an output (detection result) of an acceleration sensor worn by a target person or a sample person. Alternatively, the exercise assisting apparatus 3 may perform at least one of the above-described exercise assisting processing, pre-training processing, and additional training processing, by using motion information 3211 generated by a different apparatus from the exercise assisting apparatus 3. In such a case, the exercise assisting apparatus 3 may omit to include the motion information generation unit 311 as shown in FIG. 13 and FIG. 14.

(6) Supplementary Note

With respect to the example embodiments described above, the following Supplementary Notes will be further disclosed.

Supplementary Note 1

An exercise assisting apparatus comprising:
a division unit configured to divide sample motion information indicating motions of a sample person doing exercise into a plurality of pieces of motion element information, according to regularity of the motions of the sample person; and
a generation unit configured to generate an inference model by causing a pre-trained model to learn time-series antecedent dependency of the plurality of pieces of motion element information, the inference model inferring motions of a target person, based on target motion information indicating the motions of the target person doing exercise.

Supplementary Note 2

The exercise assisting apparatus according to supplementary note 1, wherein
the pre-trained model is a model generated through learning time-series antecedent dependency of a plurality of pieces of first motion element information that is the plurality of pieces of motion element information,
the plurality of pieces of first motion element information is generated by dividing, according to the regularity of the motions of the sample person, first sample motion information that is the sample motion information indicating the motions of the sample person doing a first type of exercise,
the division unit is configured to divide second sample motion information into a plurality of pieces of second motion element information, the second sample motion information being the sample motion information indicating the motions of the sample person doing a second type of exercise that is different from the first type of exercise, the plurality of pieces of second motion element information being the plurality of pieces of motion element information, and
the generation unit is configured to generate the inference model by causing the pre-trained model to additionally learn time-series antecedent dependency of the plurality of pieces of second motion element information.

Supplementary Note 3

The exercise assisting apparatus according to supplementary note 2, wherein
the inference model is a model inferring the motions of the target person, based on the target motion information indicating the motions of the target person doing the second type of exercise.

Supplementary Note 4

The exercise assisting apparatus according to supplementary note 2 or 3, wherein
the first sample motion information indicates exemplary motions of the sample person doing the first type of exercise, and different motions of the sample person doing the first type of exercise, the different motions being different from the exemplary motions, and
the second sample motion information indicates exemplary motions of the sample person doing the second type of exercise.

Supplementary Note 5

The exercise assisting apparatus according to any one of supplementary notes 2 to 4, wherein
the first type of exercise and the second type of exercise are exercises belonging to an identical category, and
the category is set based on a body part that is moved by exercise or a body part on which exercise places an impact.

Supplementary Note 6

The exercise assisting apparatus according to any one of supplementary notes 2 to 5, wherein
the division unit is configured to divide the first sample motion information into the plurality of pieces of first motion element information, and
the generation unit is configured to generate the pre-trained model through learning time-series antecedent dependency of the plurality of pieces of first motion element information.

Supplementary Note 7

The exercise assisting apparatus according to any one of supplementary notes 1 to 6, further comprising an inference unit configured to infer the motions of the target person by using the inference model generated by the generation unit and the target motion information.

Supplementary Note 8

An exercise assisting apparatus comprising:
an acquisition unit configured to acquire an inference model capable of inferring motions of a target person from target motion information indicating the motions of the target person doing exercise; and
an inference unit configured to infer the motions of the target person by using the inference model and the target motion information,
wherein the inference model is a model generated by dividing sample motion information indicating motions of a sample person doing exercise into a plurality of pieces of motion element information, according to a flow of changes in motion of the sample person, and by causing a pre-trained model to learn time-series antecedent dependency of the plurality of pieces of motion element information.

Supplementary Note 9

The exercise assisting apparatus according to supplementary note 8, wherein
the sample motion information indicates the motions of the sample person doing a first type of exercise, and
the target motion information indicates the motions of the target person doing a second type of exercise that is different from the first type of exercise.

Supplementary Note 10

The exercise assisting apparatus according to supplementary note 8 or 9, further comprising a display unit configured to display notification information, in a superimposing manner, on an image of the target person when the motions of the target person inferred by the inference unit are displaced from exemplary motions, the notification information notifying a body part of the target person that is displaced from the exemplary motions.

Supplementary Note 11

An exercise assisting method comprising:
dividing sample motion information indicating motions of a sample person doing exercise into a plurality of pieces of motion element information, according to regularity of the motions of the sample person; and
generating an inference model by causing a pre-trained model to learn time-series antecedent dependency of the plurality of pieces of motion element information, the inference model inferring motions of a target person, based on target motion information indicating the motions of the target person doing exercise.

Supplementary Note 12

An exercise assisting method comprising:
acquiring an inference model capable of inferring motions of a target person from target motion information indicating the motions of the target person doing exercise; and
inferring the motions of the target person by using the inference model and the target motion information,
wherein the inference model is a model generated by dividing sample motion information indicating motions of a sample person doing exercise into a plurality of pieces of motion element information, according to a flow of changes in motion of the sample person, and by causing a pre-trained model to learn time-series antecedent dependency of the plurality of pieces of motion element information.

Supplementary Note 13

A recording medium storing a computer program causing a computer to execute an exercise assisting method, the exercise assisting method including:
  dividing sample motion information indicating motions of a sample person doing exercise into a plurality of pieces of motion element information, according to regularity of the motions of the sample person; and
  generating an inference model by causing a pre-trained model to learn time-series antecedent dependency of the plurality of pieces of motion element information, the inference model inferring motions of a target person, based on target motion information indicating the motions of the target person doing exercise.

Supplementary Note 14

A recording medium storing a computer program causing a computer to execute an exercise assisting method,
  the exercise assisting method including:
  acquiring an inference model capable of inferring motions of a target person from target motion information indicating the motions of the target person doing exercise; and
  inferring the motions of the target person by using the inference model and the target motion information,
  wherein the inference model is a model generated by dividing sample motion information indicating motions of a sample person doing exercise into a plurality of pieces of motion element information, according to a flow of changes in motion of the sample person, and by causing a pre-trained model to learn time-series antecedent dependency of the plurality of pieces of motion element information.

Changes can be made as appropriate to the present invention within a scope in which no contradiction occurs to the gist or the idea of the invention that can be read from claims and the specification in its entirety, and an exercise assisting apparatus, an exercise assisting method, and a recording medium involving such changes are also included in the technical idea of the present invention.

BRIEF DESCRIPTION OF REFERENCE NUMBERS

SYS Exercise assisting system
1 Color image collection apparatus
2 Distance image collection apparatus
3 Exercise assisting apparatus
31 Computation apparatus
311 Motion information generation unit
312 Element division unit
313 Motion inference unit
314 Model generation unit
32 Storage apparatus
321 Motion information DB
3211 Motion information
3214 Motion element information
323 Training dataset
3231 Motion information
3232 Ground truth label
3235 Motion element information

The invention claimed is:

1. An exercise assisting apparatus comprising:
  at least one memory configured to store instructions; and
  at least one processor configured to execute the instructions to:
  divide sample motion information indicating motions of a sample person repeating same exercise into a plurality of pieces of motion element information, according to regularity of the motions of the sample person;
  generate an inference model by causing a pre-trained model to learn time-series antecedent dependency of the plurality of pieces of motion element information by machine learning, the inference model inferring motions of a target person, based on target motion information indicating the motions of the target person doing exercise;
  acquire one or more images of the target person who is repeating same exercise from an image pickup apparatus;
  divide motions of the target person in the acquired one or more images into a plurality of pieces of motion element information;
  infer a difference between the motions of the target person and exemplary motions by sing the inference model based on the plurality of pieces of motion element information; and
  display the inferred difference in a superimposed manner on an image in which the target person appears.

2. The exercise assisting apparatus according to claim 1, wherein
  the at least one processor is configured to execute the instructions to:
  display an object and a text message indicating a body part of the target person that is displaced from the exemplary motions, as the inferred difference.

3. The exercise assisting apparatus according to claim 1, wherein
  the inferred difference is inferred based on a difference between a vector indicating the exemplary motions and a vector indicating the motions of the target person.

4. The exercise assisting apparatus according to claim 1, wherein
  the pre-trained model is a model generated through learning time-series antecedent dependency of a plurality of pieces of first motion element information that is the plurality of pieces of motion element information,
  the plurality of pieces of first motion element information is generated by dividing, according to the regularity of the motions of the sample person, first sample motion information that is the sample motion information indicating the motions of the sample person doing a first type of exercise,
  the at least one processor is configured to execute the instructions to:
  divide second sample motion information into a plurality of pieces of second motion element information, the second sample motion information being the sample motion information indicating the motions of the sample person doing a second type of exercise that is different from the first type of exercise, the plurality of pieces of second motion element information being the plurality of pieces of motion element information, and
  generate the inference model by causing the pre-trained model to additionally learn time-series antecedent dependency of the plurality of pieces of second motion element information.

5. The exercise assisting apparatus according to claim 2, wherein
  the at least one processor is configured to execute the instructions to:
  output notification information in the superimposing manner on the image of the target person, the notification information notifying a body part of the target person that is displaced from the exemplary motions.

6. The exercise assisting apparatus according to claim 4, wherein the at least one processor is configured to execute the instructions to display the notification information to optimize the motions of the target person so that the motions of the target person is closer to the exemplary motions.

7. The exercise assisting apparatus according to claim 1, wherein the target person is a person who is exercising with a support by a doctor, a nurse, or a physical therapist.

8. An exercise assisting method comprising:

dividing sample motion information indicating motions of a sample person repeating same exercise into a plurality of pieces of motion element information, according to regularity of the motions of the sample person;

generating an inference model by causing a pre-trained model to learn time-series antecedent dependency of the plurality of pieces of motion element information by machine learning, the inference model inferring motions of a target person, based on target motion information indicating the motions of the target person doing exercise;

acquiring one or more images of the target person who is repeating same exercise from an image pickup apparatus;

dividing motions of the target person in the acquired one or more images into a plurality of pieces of motion element information;

inferring a difference between the motions of the target person and exemplary motions by sing the inference model based on the plurality of pieces of motion element information; and displaying the inferred difference in a superimposed manner on an image in which the target person appears.

9. A non-transitory recording medium storing a computer program causing a computer to execute an exercise assisting method, the exercise assisting method including:

dividing sample motion information indicating motions of a sample person repeating same exercise into a plurality of pieces of motion element information, according to regularity of the motions of the sample person;

generating an inference model by causing a pre-trained model to learn time-series antecedent dependency of the plurality of pieces of motion element information by machine learning, the inference model inferring motions of a target person, based on target motion information indicating the motions of the target person doing exercise;

acquiring one or more images of the target person who is repeating same exercise from an image pickup apparatus;

dividing motions of the target person in the acquired one or more images into a plurality of pieces of motion element information;

inferring a difference between the motions of the target person and exemplary motions by sing the inference model based on the plurality of pieces of motion element information; and displaying the inferred difference in a superimposed manner on an image in which the target person appears.

* * * * *